United States Patent
Zoellner

(10) Patent No.: US 10,069,078 B2
(45) Date of Patent: Sep. 4, 2018

(54) SEMICONDUCTING MATERIAL COMPRISING AZA-SUBSTITUTED PHOSPHINE OXIDE MATRIX AND METAL SALT

(71) Applicant: Novaled GmbH, Dresden (DE)

(72) Inventor: Mike Zoellner, Dresden (DE)

(73) Assignee: NOVALED GMBH, Dresden (DE)

( * ) Notice: Subject to any disclaimer, the term of this patent is extended or adjusted under 35 U.S.C. 154(b) by 387 days.

(21) Appl. No.: 14/782,721

(22) PCT Filed: Apr. 9, 2014

(86) PCT No.: PCT/EP2014/057193
§ 371 (c)(1),
(2) Date: Oct. 6, 2015

(87) PCT Pub. No.: WO2014/167020
PCT Pub. Date: Oct. 16, 2014

(65) Prior Publication Data
US 2016/0111654 A1  Apr. 21, 2016

(30) Foreign Application Priority Data
Apr. 10, 2013  (EP) .................................... 13163030

(51) Int. Cl.
*H01L 51/50* (2006.01)
*H01L 51/00* (2006.01)
(Continued)

(52) U.S. Cl.
CPC ........ *H01L 51/0067* (2013.01); *C07F 9/5728* (2013.01); *C07F 9/587* (2013.01);
(Continued)

(58) Field of Classification Search
None
See application file for complete search history.

(56) References Cited

U.S. PATENT DOCUMENTS

| 5,093,698 A | 3/1992 | Egusa |
| 7,074,500 B2 | 7/2006 | Pfeiffer et al. |

(Continued)

FOREIGN PATENT DOCUMENTS

| JP | 2002063989 A | 2/2002 |
| JP | 2004204140 A | 7/2004 |

(Continued)

OTHER PUBLICATIONS

PCT International Search Report for PCT Application No. PCT/EP2014/057193 dated Jul. 10, 2014 (3 pages).
(Continued)

*Primary Examiner* — Gregory D Clark
(74) *Attorney, Agent, or Firm* — Eversheds Sutherland (US) LLP

(57) ABSTRACT

The present invention relates to a semiconducting material including at least one salt or complex of a metal cation and an aza-substituted phosphine oxide compound with improved electrical properties, and to a compound suitable for this organic semiconducting material and an electronic device utilizing the improved electrical properties of the semiconducting material.

15 Claims, 19 Drawing Sheets

(51) Int. Cl.
*C07F 9/572* (2006.01)
*C07F 9/58* (2006.01)
*C07F 9/6512* (2006.01)
*C07F 9/6558* (2006.01)

(52) U.S. Cl.
CPC ...... *C07F 9/65126* (2013.01); *C07F 9/65583* (2013.01); *H01L 51/0054* (2013.01); *H01L 51/0058* (2013.01); *H01L 51/0072* (2013.01); *H01L 51/0077* (2013.01); H01L 51/5004 (2013.01); H01L 51/5076 (2013.01); H01L 2251/552 (2013.01)

(56) References Cited

U.S. PATENT DOCUMENTS

| | | | |
|---|---|---|---|
| 8,722,208 | B2 | 5/2014 | Kai et al. |
| 2008/0203406 | A1 | 8/2008 | He et al. |
| 2008/0227979 | A1 | 9/2008 | Saalbeck et al. |
| 2009/0009072 | A1 | 1/2009 | Wellmann et al. |
| 2009/0045728 | A1 | 2/2009 | Murano et al. |
| 2010/0288362 | A1 | 11/2010 | Hatwar et al. |
| 2012/0261651 | A1 | 10/2012 | Noto et al. |

FOREIGN PATENT DOCUMENTS

| | | | | |
|---|---|---|---|---|
| JP | 2009-023914 A | | 2/2009 | |
| JP | 2010-278376 | * | 12/2010 | ............ H01L 51/50 |
| JP | 2010-0278376 A | | 12/2010 | |
| WO | 2013/079676 A1 | | 6/2013 | |
| WO | 2013/079678 A1 | | 6/2013 | |

OTHER PUBLICATIONS

Bard and Faulkner, Electrochemical Methods, Chapter 1: Introduction and Overview of Electrode Processes, p. 128; Section 6.5, p. 239-247, 2nd Edition, 2000.

Connelly et al., "Chemical Redox Agents for Organometallic Chemistry," Chem. Rev., 1996, 96:877-910.

D'Andrade et al., "Relationship Between the Ionization and Oxidation Potentials of Molecular Organic Semiconductors," Organic Electronics, 2005, 6:11-20.

Tang et al., "Organic Electroluminiscent Diodes," Appl. Phys. Lett., 1987, 51(12):913-915.

Wu et al., "Computational Design of Host Materials Suitable for Green-(Deep) Blue Phosphors through Effectively Tuning the Triplet Energy While Maintaining the Ambipolar Property," J. Phys. Chem. C., 2013, 117:8420-8428.

Chinese Office Action for CN Application No. 201480026578.2 dated Apr. 5, 2017 (Englis translation) (14 pages).

* cited by examiner

SEMICONDUCTING MATERIAL COMPRISING AZA-SUBSTITUTED PHOSPHINE OXIDE MATRIX AND METAL SALT

CROSS REFERENCE TO RELATED APPLICATIONS

This application is a U.S. national stage application of PCT/EP2014/057193, filed Apr. 9, 2014, which claims priority to European Application No. 13163030.3, filed Apr. 10, 2013. The contents of these applications are hereby incorporated by reference.

The present invention concerns organic semiconducting material with improved electrical properties, and compound suitable for this organic semiconducting material and electronic device utilizing the improved electrical properties of the inventive semiconducting material.

BACKGROUND OF THE INVENTION

Among the electronic devices comprising at least a part based on material provided by organic chemistry, organic light emitting diodes (OLEDs) have a prominent position. Since the demonstration of efficient OLEDs by Tang et al. in 1987 (C. W. Tang et al., Appl. Phys. Lett. 51 (12), 913 (1987)), OLEDs developed from promising candidates to high-end commercial displays. An OLED comprises a sequence of thin layers substantially made of organic materials. The layers typically have a thickness in the range of 1 nm to 5 µm. The layers are usually formed either by means of vacuum deposition or from a solution, for example by means of spin coating or jet printing.

OLEDs emit light after the injection of charge carriers in the form of electrons from the cathode and in form of holes from the anode into organic layers arranged in between. The charge carrier injection is effected on the basis of an applied external voltage, the subsequent formation of excitons in a light emitting zone and the radiative recombination of those excitons. At least one of the electrodes is transparent or semitransparent, in the majority of cases in the form of a transparent oxide, such as indium tin oxide (ITO), or a thin metal layer.

It is an objective of the invention to overcome the drawbacks of the prior art and to provide compounds which can be successfully embedded in electrically doped semiconducting materials for use in electronic devices. The inventive semiconducting materials shall afford devices with better characteristics, especially with low voltage and, more specifically, OLEDs with higher efficiency.

SUMMARY OF THE INVENTION

The object is achieved by semiconducting material comprising at least one salt or complex of a metal cation and a compound according to formula (I):

wherein $R^1$, $R^2$ and $R^3$ are independently selected from $C_1$-$C_{30}$-alkyl, $C_3$-$C_{30}$ cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, $C_6$-$C_{30}$-aryloxy, and from structural unit having general formula E-A-, wherein A is a spacer unit containing trivalent nitrogen atom bearing a lone electron pair, wherein the spacer unit has a structure which allows formation of a 5-, 6- or 7-membered chelate ring with the metal cation, wherein the chelate ring comprises the oxygen atom of the phosphine oxide group and trivalent nitrogen atom of the spacer unit coordinated to the metal cation and E is an electron transporting unit comprising a conjugated system of at least 10 delocalized electrons, and at least one group selected from $R^1$, $R^2$ and $R^3$ has the general formula E-A-.

The salt or complex of a metal cation works in the inventive semiconducting material as an electrical dopant, whereas the compound of formula (I) has the function of a charge transporting matrix.

Examples of conjugated systems of delocalized electrons are systems of alternating pi- and sigma bonds. Optionally, one or more two-atom structural units having the pi-bond between its atoms can be replaced by an atom bearing at least one lone electron pair, typically by a divalent atom selected from O, S, Se, Te or by a trivalent atom selected from N, P, As, Sb, Bi. Preferably, the conjugated system of delocalized electrons comprises at least one aromatic ring adhering to the Hückel rule. More preferably, the conjugated system of delocalized electrons comprises a condensed aromatic skeleton comprising at least 10 delocalized electrons, e.g. a naphthalene, anthracene, phenanthrene, pyrene, quinoline, indole or carbazole skeleton. Also preferably, the conjugated system of delocalized electrons may consist of at least two directly attached aromatic rings, the simplest examples of such systems being biphenyl, bithienyl, phenylthiophene, phenylpyridine and like.

It is preferable that the lowest unoccupied molecular orbital (LUMO) of the compound (I) is localized mainly on its electron transporting units E. The presence of at least 10 delocalized electrons in the conjugated system makes the lowest unoccupied molecular orbital of the whole compound of formula (I) localized mainly on the electron transporting unit E.

More specifically, the localization of a frontier orbital like LUMO in the molecule can be assigned by a skilled person to that part of the molecule which contains the largest conjugated pi-electron system. In case that two or more pi-electron systems with the same extent (given by the number of pi electrons in conjugation) occur in the molecule, the lowest energy can be assigned to the system linked with strongest electron withdrawing groups and/or weakest electron donating groups. The electron withdrawing and/or electron accepting effects of various substituents are commensurate to experimentally accessible parameters like Hammet or Taft constants which are tabulated for large number of substituents most frequently occurring in aromatic or heteroaromatic organic compounds. In most cases, the above mentioned parameters are sufficient for a reliable LUMO localization, because the overall effect of more substituents attached to the same aromatic system is additive. In case of uncertainty, the ultimate method for the correct LUMO localization in the molecule is quantum chemical calculation. Reliable results with relatively low demand for computational capacity provide for example the methods based on density functional theory (DFT methods).

It is desirable that the LUMO level of compound (I), measured by cyclic voltammetry (CV) against ferrocenium/ferrocene redox couple in tetrahydrofuran (THF) as a reference, is in the range −1.8--−3.1 V. It is preferred that the energy of this LUMO is in the range −2.0--−2.9 V, more preferably in the range −2.15--−2.75 V, even more preferably in the range −2.3--−2.6 V. Modern quantum chemical methods allow also a reliable estimation of relative LUMO energies for different molecules. The computed relative values can be recalculated to absolute scale corresponding to the electrochemical potentials measured in a concrete CV experimental setting, if the calculated value is compared with the value measured for the same compound and the obtained difference is taken into account as a correction for the values calculated for other compounds.

Preferably, the semiconducting material comprising the compound of formula I and metal salt serves as an electron transporting material or as an electron injecting material.

If not explicitly stated that a group or structural unit is unsubstituted, the given count of atoms (e.g., given count of carbon atoms) comprises also possible substituents.

It is preferred that the metal cation is the cation of a monovalent or divalent metal; in other words, cations bearing only one or two elementary charges are preferred.

It is further preferred that the metal cation is a cation of an element selected from the main groups of the Periodic Table, more preferably from the first or second main group of the Periodic Table. Also preferably, the metal salt has a formula selected from $M^1Z^1$, $M^2Z^2$ and $M^2(Z^1)_2$, wherein $M^1$ is metal cation bearing one elemental charge, $M^2$ is a double charged metal cation, $Z^1$ is a single charged anion and $Z^2$ is a double-charged anion. Most preferably, the metal salt or complex is a salt or complex of $Li^+$ or $Mg^{2+}$.

It is further preferred that the spacer A is a divalent six-membered aromatic heterocyclic group. More preferably, the spacer A is selected from azine-2,4-diyl, azine-2,5-diyl, azine-2,6-diyl, 1,3-diazine-2,4-diyl and 1,3-diazine-2,5-diyl. Even preferably, the electron transporting unit E is a $C_{14}$-$C_{50}$ aryl or heteroaryl. Examples of an appropriate electron transporting unit are aryls and heteroaryls (arene or heteroarene radicals comprising at least two condensed aromatic rings). The term radical means an organic residue derived from an organic molecule by a formal hydrogen abstraction.

Preferably, the electron transporting unit E comprises an aromatic or heteroaromatic skeleton having 2-5 condensed aromatic rings. More specifically, examples of the preferable electron transporting units are naphtyl, anthracenyl, phenanthrenyl, pyrenyl, quinolinyl. 1,1'-biphenylyl is also preferable, although its rings are not condensed. Both the spacer A as well as the electron transporting unit E may be unsubstituted or appropriately substituted by electron withdrawing or electron donating groups which allow further tuning of the frontier orbital energy levels of the molecule. Typical examples of electron withdrawing groups are phenyl, halogen, carbonyl, nitrile, haloalkyl or haloaryl groups and six-membered nitrogen-containing heterocyclic radicals like pyridyl, diazinyl or triazinyl. Halogen means fluorine, chlorine, bromine or iodine; specific examples of haloalkyl and haloaryl groups are perhaloalkyl and perhaloaryl groups, like trichloromethyl, trifluoromethyl, pentafluoroethyl, heptafluoroisopropyl, perfluoro-tert-butyl or pentafluorophenyl. Examples of electron donating groups are alkyl groups like methyl, ethyl, propyl, isopropyl, heteroalkyl groups wherein one or more non-adjacent methylene units in the alkyl chain are replaced by a heteroatom, alkoxy groups, alkylthio groups, and five-membered heterocycles comprising up to three heteroatoms selected from N, O and S. Typical examples of heteroatoms comprised in heteroalkyls are O, S and Si, represented by ether, sulphide or dialkylsilylene groups. Cycloalkyl has the meaning of a hydrocarbyl substituent which comprises at least one carbocyclic structure which is not aromatic. It is understood that the terms alkyl and cycloalkyl comprise also unsaturated and branched hydrocarbyl groups.

It is preferred that at least one of $R^1$, $R^2$ and $R^3$ is a group represented by formula

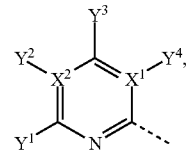

wherein the dashed line means the single bond to the phosphorus atom,
$Y^1$ and $Y^3$ are independently selected from H, $C_6$-$C_{50}$ aryl, $C_3$-$C_{50}$ heteroaryl, $P(O)R^4R^5$;
$Y^2$ and $Y^4$ are independently selected from H, $C_6$-$C_{50}$ aryl and $C_3$-$C_{50}$ heteroaryl;
$R^4$ and $R^5$ are independently selected from $C_6$-$C_{30}$ aryl, $C_3$-$C_{30}$ cycloalkyl and $C_3$-$C_{30}$ heteroaryl,
$X^1$ and $X^2$ are independently selected from C and N.

Preferably, both $X^1$ and $X^2$ are not N at the same time. Even preferably, none of $Y^1$ and $Y^3$ is $P(O)R^4R^5$ if any of $X^1$ and $X^2$ is N. Even preferably, at least one of $Y^1$, $Y^2$, $Y^3$, $Y^4$ is 1,1'-biphenylyl or comprises at least two condensed aromatic rings. Also preferably, at least one of $Y^1$, $Y^2$, $Y^3$, $Y^4$ is selected from naphtyl, 1,1'-biphenylyl, quinolinyl, anthracenyl, phenanthrenyl, pyrenyl.

It is further preferred that the compound of formula (I) has the structure (Ia) or (Ib)

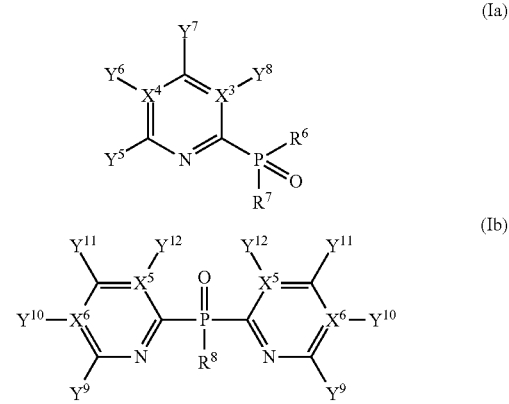

wherein $R^6$, $R^7$ and $R^8$ are independently selected from $C_6$-$C_{30}$ aryl, $C_3$-$C_{30}$ cycloalkyl and $C_3$-$C_{30}$ heteroaryl,
$Y^5$, $Y^7$, $Y^9$ and $Y^{11}$ are independently selected from H, $C_6$-$C_{50}$ aryl, $C_3$-$C_{50}$ heteroaryl and $P(O)R^4R^5$,
$Y^6$, $Y^8$, $Y^{10}$ and $Y^{12}$ are independently selected from H, $C_6$-$C_{50}$ aryl and $C_3$-$C_{50}$ heteroaryl,
$X^3$, $X^4$, $X^5$ and $X^6$ are independently selected from C and N, with the proviso that
  i) both $X^3$ and $X^4$ or both $X^5$ and $X^6$ are not N at the same time and if any of $X^3$ and $X^4$ or any of $X^5$ and $X^6$ is N, the adjacent Y is an electron lone pair
  ii) neither $Y^5$ nor $Y^7$ and neither $Y^9$ nor $Y^{11}$ is $P(O)R^4R^5$ if any of $X^3$ and $X^4$ or any of $X^5$ and $X^6$ is N, and iii) at least one of $Y^5$, $Y^6$, $Y^7$, $Y^8$ and at least one of $Y^9$, $Y^{10}$, $Y^{11}$, $Y^{12}$ is 1,1'-biphenylyl or comprises at least two condensed aromatic rings.

It is advantageous if at least one of Y groups bound to the same heterocyclic ring in the structure (Ia) or (Ib) comprises 2-5 condensed aromatic rings. 1,1'-biphenylyl is also preferable, although its rings are not condensed. More preferably, at least one of Y groups bound to the same heterocyclic ring in the structure (Ia) or (Ib) comprises anthracene, phenanthrene or pyrene skeleton.

Also preferably, at least one of $Y^5$-$Y^8$ in formula (Ia) or at least one of $Y^8$-$Y^{11}$ in formula (Ib) is selected from naphtyl, 1,1'-biphenylyl, quinolinyl, anthracenyl, phenanthrenyl, pyrenyl.

It is preferred that the semiconducting material according to the invention comprises the salt or complex of a metal cation and a compound according to formula (I) at least partly in form of a homogeneous mixture, wherein both components are molecularly dispersed in each other.

Another object the invention is achieved by an electronic device comprising at least one semiconducting material according to the invention, preferably in form of an electronic device wherein the inventive semiconducting material forms at least one layer between a cathode and an anode.

Specifically, the second object of the invention is represented by an electronic device comprising at least one semiconducting layer comprising the semiconducting material according to the invention or consisting of it. More specifically, the semiconducting material according to the invention is used in the electronic device as an electron transporting layer, as an electron injecting layer, or as a layer having double electron transporting and hole blocking function.

In specific cases, also exciton blocking function can be considered.

Preferably, the arrangement of the inventive device does not allow that the inventive semiconducting layer emits light. In other words, it is preferred that only electrons enter the inventive semiconducting layer, whereas the access of holes is blocked, preventing thus exciton formation.

Another object of the invention is compound having the structure according to formula (I)

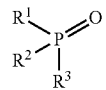

wherein $R^1$, $R^2$ and $R^3$ are independently selected from $C_1$-$C_{30}$-alkyl, $C_3$-$C_{30}$-cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, $C_6$-$C_{30}$-aryloxy,
at least one of $R^1$, $R^2$ and $R^3$ is a group represented by formula

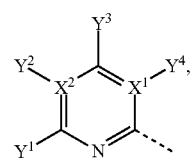

the dashed line means the single bond to the phosphorus atom, $Y^1$ and $Y^3$ are independently selected from H, $C_6$-$C_{50}$ aryl, $C_3$-$C_{50}$ heteroaryl, $P(O)R^4R^5$;
$Y^2$ and $Y^4$ are independently selected from H, $C_6$-$C_{50}$ aryl and $C_3$-$C_{50}$ heteroaryl;
$R^4$ and $R^5$ are independently selected from $C_6$-$C_{30}$ aryl, $C_3$-$C_{30}$ cycloalkyl and $C_3$-$C_{30}$ heteroaryl,
$X^1$ and $X^2$ are independently selected from C and N, with the proviso that
i) both $X^1$ and $X^2$ are not N at the same time and if any of $X^1$ and $X^2$ is N, the adjacent Y is an electron lone pair
ii) none of $Y^1$ and $Y^3$ is $P(O)R^4R^5$ if any of $X^1$ and $X^2$ is N, and
iii) at least one of $Y^1$, $Y^2$, $Y^3$, $Y^4$ is 1,1'-biphenylyl or comprises at least two condensed aromatic rings.

It is further preferred that the compound of formula (I) has the structure (Ia) or (Ib)

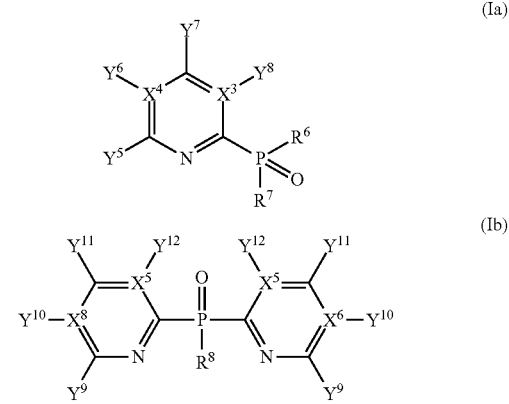

wherein $R^6$, $R^7$ and $R^8$ are independently selected from $C_6$-$C_{30}$ aryl, $C_3$-$C_{30}$ cycloalkyl and $C_3$-$C_{30}$ heteroaryl,
$Y^5$, $Y^7$, $Y^9$ and $Y^{11}$ are independently selected from H, $C_6$-$C_{50}$ aryl, $C_3$-$C_{50}$ heteroaryl and $P(O)R^4R^5$,
$Y^6$, Y, $Y^{10}$ and $Y^{12}$ are independently selected from H, $C_6$-$C_{50}$ aryl and $C_3$-$C_{50}$ heteroaryl,
$X^3$, $X^4$, $X^5$ and $X^6$ are independently selected from C and N, with the proviso that
i) both $X^3$ and $X^4$ or both $X^5$ and $X^6$ are not N at the same time and if any of $X^3$ and $X^4$ or any of $X^5$ and $X^6$ is N, the adjacent Y is an electron lone pair
ii) neither $Y^5$ nor $Y^7$ and neither $Y^9$ nor $Y^{11}$ is $P(O)R^4R^5$ if any of $X^3$ and $X^4$ or any of $X^5$ and $X^6$ is N, and
iii) at least one of $Y^5$, $Y^6$, $Y^7$, $Y^8$ and at least one of $Y^9$, $Y^{10}$, $Y^{11}$, $Y^{12}$ is 1,1'-biphenylyl or comprises at least two condensed aromatic rings.

It is advantageous if at least one of Y groups bound to the same heterocyclic ring in the structure (Ia) or (Ib) is 1,1'-biphenylyl or comprises 2-5 condensed aromatic rings. More preferably, at least one of Y groups bound to the same heterocyclic ring in the structure (Ia) or (Ib) comprises anthracene, phenanthrene or pyrene skeleton. Also preferably, at least one of $Y^5$, $Y^6$, $Y^7$, $Y^8$ or at least one of $Y^9$, $Y^{10}$, $Y^{11}$, $Y^{12}$ is selected from naphtyl, 1,1'-biphenylyl, quinolinyl, anthracenyl, phenanthrenyl, pyrenyl.

III. BRIEF DESCRIPTION OF THE DRAWINGS

DETAILED DESCRIPTION OF THE INVENTION

Device Architecture

Figure 1:
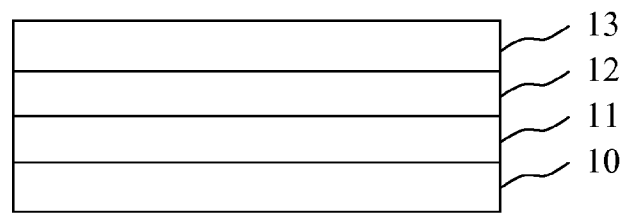
FIG. 1 shows a schematic illustration of a device in which the present invention can be incorporated.

FIG. 1 shows a stack of anode (10), organic semiconducting layer (11) comprising the light emitting layer, electron transporting layer (ETL) (12), and cathode (13). Other layers can be inserted between those depicted, as explained herein.

Figure 2:
FIG. 2 shows a schematic illustration of a device in which the present invention can be incorporated.

FIG. 2 shows a stack of an anode (20), a hole injecting and transporting layer (21), a hole transporting layer (22) which can also aggregate the function of electron blocking, a light emitting layer (23), an ETL (24), and a cathode (25). Other layers can be inserted between those depicted, as explained herein.

The wording "device" comprises the organic light emitting diode.

Material Properties—Energy Levels

A method to determine the ionization potentials (IP) is the ultraviolet photo spectroscopy (UPS). It is usual to measure the ionization potential for solid state materials; however, it is also possible to measure the IP in the gas phase. Both values are differentiated by their solid state effects, which are, for example the polarization energy of the holes that are created during the photo ionization process. A typical value for the polarization energy is approximately 1 eV, but larger discrepancies of the values can also occur. The IP is related to beginning of the photoemission spectra in the region of the large kinetic energy of the photoelectrons, i.e. the energy of the most weakly bounded electrons. A related method to UPS, the inverted photo electron spectroscopy (IPES) can be used to determine the electron affinity (EA). However, this method is less common. Electrochemical measurements in solution are an alternative to the determination of solid state oxidation ($E_{ox}$) and reduction ($E_{red}$) potential. An adequate method is for example the cyclo-voltammetry. A simple rule is used very often for the conversion of red/ox potentials into electron affinities and ionization potential: IP=4.8 eV+e*$E_{ox}$ (vs. ferrocenium/ferrocene (Fc$^+$/Fc)) and EA=4.8 eV+e*$E_{red}$ (vs. Fc$^+$/Fc) respectively (see B. W. D'Andrade, Org. Electron. 6, 11-20 (2005)). Processes are known for the correction of the electrochemical potentials in the case other reference electrodes or other redox pairs are used (see A. J. Bard, L. R. Faulkner, "Electrochemical Methods: Fundamentals and Applications", Wiley, 2. Ausgabe 2000). The information about the influence of the solution used can be found in N. G. Connelly et al., Chem. Rev. 96, 877 (1996). It is usual, even if not exactly correct to use the terms, "energy of the HOMO" $E_{(HOMO)}$ and "energy of the LUMO" $E_{(LUMO)}$ respectively as synonyms for the ionization energy and electron affinity (Koopmans Theorem). It has to be taken in consideration, that the ionization potentials and the electron affinities are given in such a way that a larger value represents a stronger binding of a released or respectively of an absorbed electron. The energy scale of the frontier molecular orbitals (HOMO, LUMO) is opposed to this. Therefore, in a rough approximation, is valid: IP=-$E_{(HOMO)}$ and EA=$E_{(LUMO)}$. The given potentials correspond to the solid-state potentials.

Substrate

It can be flexible or rigid, transparent, opaque, reflective, or translucent. The substrate should be transparent or translucent if the light generated by the OLED is to be transmitted through the substrate (bottom emitting). The substrate may be opaque if the light generated by the OLED is to be emitted in the direction opposite of the substrate, the so called top-emitting type. The OLED can also be transparent. The substrate can be either arranged adjacent to the cathode or anode.

Electrodes

The electrodes are the anode and the cathode, they must provide a certain amount of conductivity, being preferentially conductors. Preferentially the "first electrode" is the cathode. At least one of the electrodes must be semi-transparent or transparent to enable the light transmission to the outside of the device. Typical electrodes are layers or a stack of layer, comprising metal and/or transparent conductive oxide. Other possible electrodes are made of thin busbars (e.g. a thin metal grid) wherein the spaces between the busbars is filled (coated) with a transparent material with a certain conductivity, such as graphene, carbon nanotubes, doped organic semiconductors, etc.

In one mode, the anode is the electrode closest to the substrate, which is called non-inverted structure. In another mode, the cathode is the electrode closest to the substrate, which is called inverted structure.

Typical materials for the Anode are ITO and Ag. Typical materials for the cathode are Mg:Ag (10 vol. % of Mg), Ag, ITO, Al. Mixtures and multilayer are also possible.

Preferably, the cathode comprises a metal selected from Ag, Al, Mg, Ba, Ca, Yb, In, Zn, Sn, Sm, Bi, Eu, Li, more preferably from Al, Mg, Ca, Ba and even more preferably selected from Al or Mg. Preferred is also a cathode comprising an alloy of Mg and Ag.

Hole-Transporting Layer (HTL)

Is a layer comprising a large gap semiconductor responsible to transport holes from the anode or holes from a CGL to the light emitting layer (LEL). The HTL is comprised between the anode and the LEL or between the hole generating side of a CGL and the LEL. The HTL can be mixed with another material, for example a p-dopant, in which case it is said the HTL is p-doped. The HTL can be comprised by several layers, which can have different compositions. P-doping the HTL lowers its resistivity and avoids the respective power loss due to the otherwise high resistivity of the undoped semiconductor. The doped HTL can also be used as optical spacer, because it can be made very thick, up to 1000 nm or more without significant increase in resistivity.

Suitable hole transport materials (HTM) can be, for instance HTM from the diamine class, where a conjugated system is provided at least between the two diamine nitrogens. Examples are N4,N4'-di(naphthalen-1-yl)-N4,N4'-diphenyl-[1,1'-biphenyl]-4,4'-diamine (HTM1), N4,N4,N4'',N4''-tetra([1,1'-biphenyl]-4-yl)-[1,1':4',1''-terphenyl]-4,4''-diamine (HTM2). The synthesis of diamines is well described in literature; many diamine HTMs are readily commercially available.

Hole-Injecting Layer (HIL)

Is a layer which facilitates the injection of holes from the anode or from the hole generating side of a CGL into an adjacent HTL. Typically the HIL is a very thin layer (<10 nm). The hole injection layer can be a pure layer of p-dopant and can be about 1 nm thick. When the HTL is doped, an HIL may not be necessary, since the injection function is already provided by the HTL.

Light-Emitting Layer (LEL)

The light emitting layer must comprise at least one emission material and can optionally comprise additional layers. If the LEL comprises a mixture of two or more materials the charge carrier injection can occur in different materials for instance in a material which is not the emitter, or the charge carrier injection can also occur directly into the emitter. Many different energy transfer processes can occur inside the LEL or adjacent LELs leading to different types of emission. For instance excitons can be formed in a host material and then be transferred as singlet or triplet excitons to an emitter material which can be singlet or triplet emitter which then emits light. A mixture of different types of emitter can be provided for higher efficiency. Mixed light can be realized by using emission from an emitter host and an emitter dopant.

Blocking layers can be used to improve the confinement of charge carriers in the LEL, these blocking layers are further explained in U.S. Pat. No. 7,074,500 B2.

Electron-Transporting Layer (ETL)

Is a layer comprising a large gap semiconductor responsible to transport electrons from the cathode or electrons from a CGL or EIL (see below) to the light emitting layer (LEL). The ETL is comprised between the cathode and the LEL or between the electron generating side of a CGL and the LEL. The ETL can be mixed with an electrical n-dopant, in which case it is said the ETL is n-doped. The ETL can be comprised by several layers, which can have different compositions. Electrical n-doping the ETL lowers its resistivity and/or improves its ability to inject electrons into an adjacent layer and avoids the respective power loss due to the otherwise high resistivity (and/or bad injection ability) of the undoped semiconductor. The doped ETL can also be used as optical spacer, because it can be made very thick, up to 1000 nm or more without significant increase in resistivity.

The present invention also employs a compound according to formula 1 in the ETL, which compound can be used in combination with other materials, in the whole layer or in a sub-layer of the ETL.

Hole blocking layers and electron blocking layers can be employed as usual.

In one mode of the invention the ETL comprises 2 layers, the first ETL (ETL1) and the second ETL (ETL2), ETL1 is closer to the LEL than the ETL2. Preferentially ETL1 comprises the compound according to formula 1, even more preferably consists only of material according to formula 1. Also preferably, ETL1 is closer to the substrate than ETL2.

Alternatively or in addition, the ETL2 comprises a compound according to formula 1. Preferably, the ETL2 is electrically doped.

Optionally ETL1 and ETL2 comprise the same compound according to formula 1.

Other layers with different functions can be included, and the device architecture can be adapted as known by the skilled in the art. For example, an Electron-Injecting Layer (EIL) can be used between the cathode and the ETL. Also the EIL can comprise the inventive matrix compounds of the present application.

Charge Generation Layer (CGL)

The OLED can comprise a CGL which can be used in conjunction with an electrode as inversion contact, or as connecting unit in stacked OLEDs. A CGL can have the most different configurations and names, examples are pn-junction, connecting unit, tunnel junction, etc. Best examples are pn junctions as disclosed in US 2009/0045728 A1, US 2010/0288362 A1. Metal layers and or insulating layers can also be used.

Stacked OLEDs

When the OLED comprises two or more LELs separated by CGLs, the OLED is named a stacked OLED, otherwise it is named a single unit OLED. The group of layers between two closest CGLs or between one of the electrodes and the closest CGL is named a electroluminescent unit (ELU). Therefore a stacked OLED can be described as anode/ELU$_1$/$\{CGL_X/ELU_{1+X}\}_X$/cathode, wherein x is a positive integer and each $CGL_X$ or each $ELU_{1+X}$ can be equal or different. The CGL can also be formed by the adjacent layers of two ELUs as disclosed in US2009/0009072 A1. Further stacked OLEDs are explained e.g. in US 2009/0045728 A1, US 2010/0288362 A1, and references therein.

Deposition of Organic Layers

Any organic semiconducting layers of the inventive display can be deposited by known techniques, such as vacuum thermal evaporation (VTE), organic vapour phase deposition, laser induced thermal transfer, spin coating, blade coating, slot dye coating, inkjet printing, etc. A preferred method for preparing the OLED according to the invention is vacuum thermal evaporation.

Preferably, the ETL is formed by evaporation. When using an additional material in the ETL, it is preferred that the ETL is formed by co-evaporation of the electron transporting matrix (ETM) and the additional material. The additional material may be mixed homogeneously in the ETL. In one mode of the invention, the additional material has a concentration variation in the ETL, wherein the concentration changes in the direction of the thickness of the stack of layers. It is also foreseen that the ETL is structured in sub-layers, wherein some but not all of these sub-layers comprise the additional material.

Electrical Doping

The present invention can be used in addition or in combination with electrical doping of organic semiconducting layers.

The most reliable and at the same time efficient OLEDs are OLEDs comprising electrically doped layers. Generally, the electrical doping means improving of electrical properties, especially the conductivity and/or injection ability of a doped layer in comparison with neat charge-transporting matrix without a dopant. In the narrower sense, which is usually called redox doping or charge transfer doping, hole transport layers are doped with a suitable acceptor material (p-doping) or electron transport layers with a donor material (n-doping), respectively. Through redox doping, the density of charge carriers in organic solids (and therefore the conductivity) can be increased substantially. In other words, the redox doping increases the density of charge carriers of a semiconducting matrix in comparison with the charge carrier density of the undoped matrix. The use of doped charge-carrier transport layers (p-doping of the hole transport layer by admixture of acceptor-like molecules, n-doping of the electron transport layer by admixture of donor-like molecules) in organic light-emitting diodes is, e.g., described in US 2008/203406 and U.S. Pat. No. 5,093,698.

US2008227979 discloses in detail the charge-transfer doping of organic transport materials, with inorganic and with organic dopants. Basically, an effective electron transfer occurs from the dopant to the matrix increasing the Fermi level of the matrix. For an efficient transfer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than +0.3 eV.

Typical examples of known redox doped hole transport materials are: copperphthalocyanine (CuPc), which HOMO level is approximately −5.2 eV, doped with tetrafluoro-tetracyanoquinonedimethane (F4TCNQ), which LUMO level is about −5.2 eV; zincphthalocyanine (ZnPc) (HOMO=−5.2 eV) doped with F4TCNQ; a-NPD (N,N'-Bis(naphthalen-1-yl)-N,N'-bis(phenyl)-benzidine) doped with F4TCNQ. a-NPD doped with 2,2'-(perfluoronaphthalene-2,6-diylidene)dimalononitrile (PD1). a-NPD doped with 2,2',2"-(cyclopropane-1,2,3-triylidene)tris(2-(p-cyanotetrafluorophenyl)acetonitrile) (PD2). All p-doping in the device examples of the present application was done with 3 mol. % of PD2.

Typical examples of known redox doped electron transport materials are: fullerene C60 doped with acridine orange base (AOB); perylene-3,4,9,10-tetracarboxylic-3,4,9,10-dianhydride (PTCDA) doped with leuco crystal violet; 2,9-di(phenanthren-9-yl)-4,7-diphenyl-1,10-phenanthroline doped with tetrakis (1,3,4,6,7,8-hexahydro-2H-pyrimido[1,2-a]pyrimidinato)ditung-sten (II) (W$_2$(hpp)$_4$); naphthalene tetracarboxylic acid di-anhydride (NTCDA) doped with 3,6-bis-(dimethyl amino)-acridine; NTCDA doped with bis(ethylene-dithio)tetrathiafulvalene (BEDT-TTF).

In the present invention, classical redox dopants with high reduction strenght, expressed as a highly negative redox potential measured by cyclic voltammetry (CV) in THF vs. Fc+/Fc standard, can be successfully replaced with metal salts having no pronounced reductive properties. True mechanism how these compounds, sometimes called "electrically doping additives", contribute to the lowering of the voltage in electronic devices, is not yet known.

Typical representatives of metal salts which are effective in the present invention are salts comprising metal cations bearing one or two elementary charges. Favourably, salts of alkali metals or alkali earth metals are used. The anion of the salt is preferably an anion providing the salt with sufficient volatility, allowing its deposition under high vacuum conditions, especially in the temperature and pressure range which is comparable with the temperature and pressure range suitable for the deposition of the electron transporting matrix.

Example of such anion is 8-hydroxyquinolinolate anion. Its metal salts, for example lithium 8-hydroxyquinolinolate (LiQ) represented by the formula D1

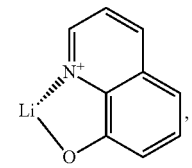

D1 are known as electrically doping additives.

Another class of metal salts useful as electrical dopants in electron transporting matrices of the present invention represent compounds disclosed in the application PCT/EP2012/074127, having general formula (II)

Formula (II)

wherein $A^1$ is a $C_6$-$C_{20}$ arylene and each of $A^2$-$A^3$ is independently selected from a $C_6$-$C_{20}$ aryl, wherein the aryl or arylene may be unsubstituted or substituted with groups comprising C and H or with a further LiO group, provided that the given C count in an aryl or arylene group includes also all substituents present on the said group. It is to be understood that the term substituted or unsubstituted arylene stands for a divalent radical derived from substituted or unsubstituted arene, wherein the both adjacent structural moieties (in formula (I), the OLi group and the diaryl prosphine oxide group) are attached directly to an aromatic ring of the arylene group. In examples of the present application, this class of dopants is represented by compound D2

D2

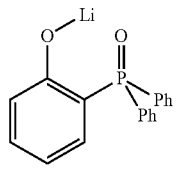

wherein Ph is phenyl.

Yet another class of metal salts useful as electrical dopants in electron transporting matrices of the present invention represent compounds disclosed in the application PCT/EP2012/074125, having general formula (III)

Formula (III)

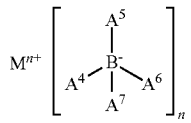

wherein M is a metal ion, each of $A^4$-$A^7$ is independently selected from H, substituted or unsubstituted $C_6$-$C_{20}$ aryl and substituted or unsubstituted $C_2$-$C_{20}$ heteroaryl and n is valency of the metal ion. In examples of the present application, this class of dopants is represented by compound D3

D3

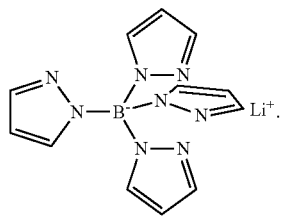

Preferred ETL matrix compounds of the present invention are

A1

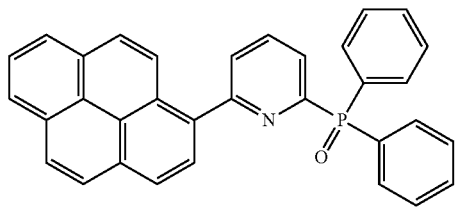

A2

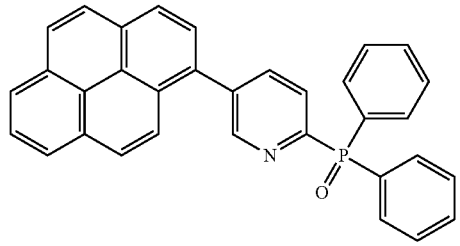

A3

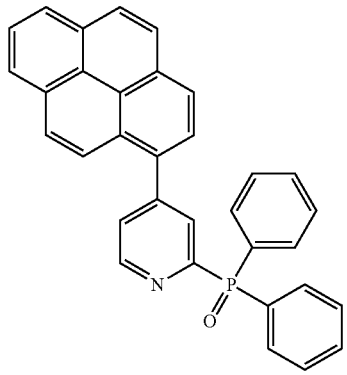

A4

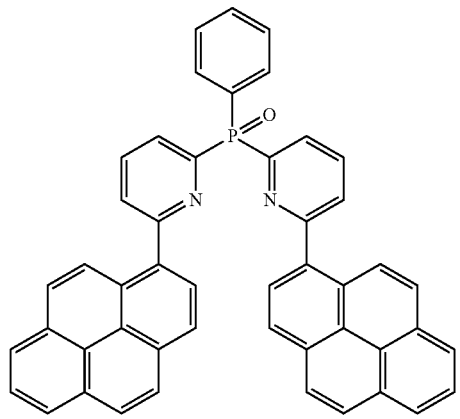

A5

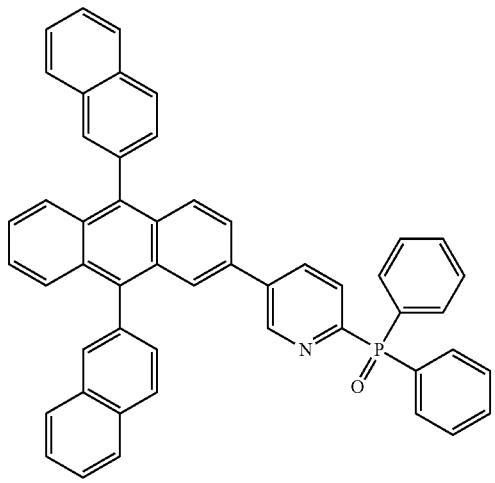

A6
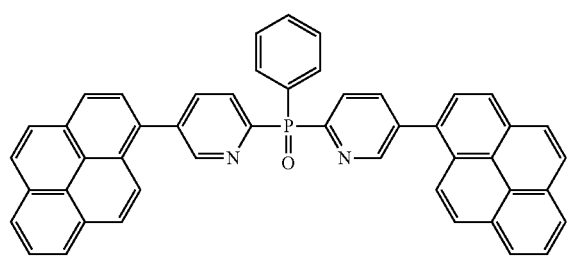

A7
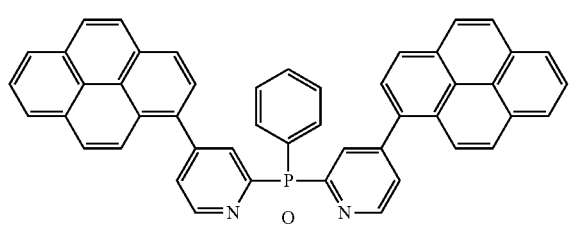

B1
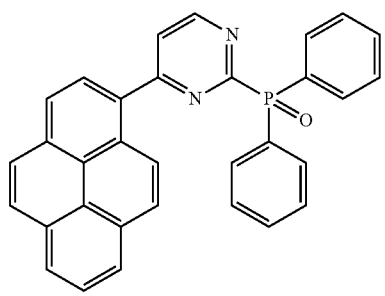

B2
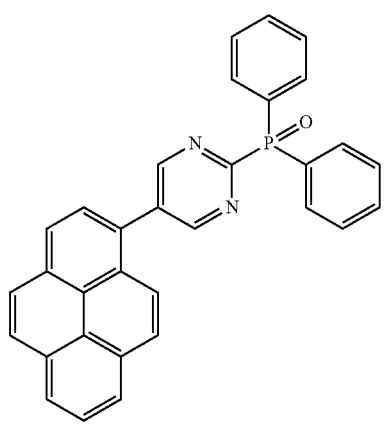

B3
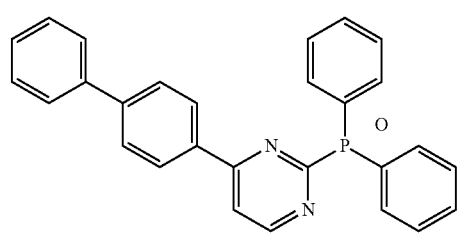

B4
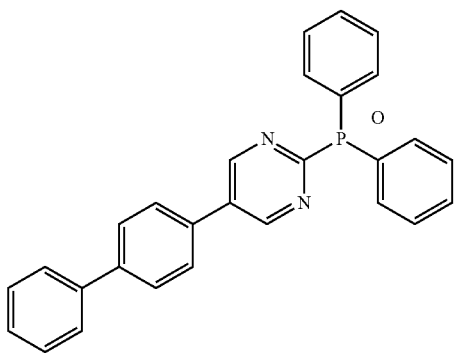

B5, B6
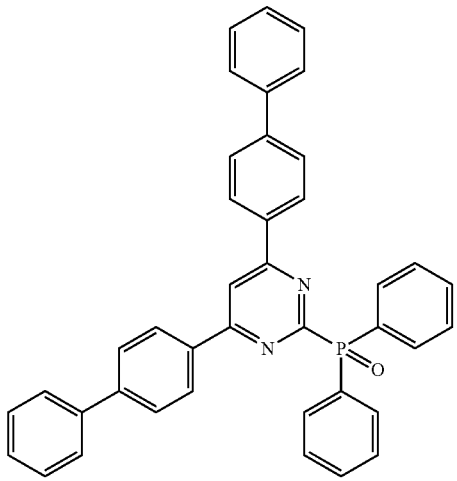

ADVANTAGEOUS EFFECT OF THE INVENTION

The favourable effects of the inventive electron-transporting matrix materials are shown in comparison with comparative devices comprising instead of the inventive compounds electron transporting matrices which lack the inventive combination of phosphine oxide group and electron transporting unit with a spacer which comprises an nitrogen atom bearing a lone electron pair in a sterical configuration allowing formation of a 5-, 6- or 7-membered chelate ring with the metal cation, wherein the chelate ring comprises the oxygen atom of the phosphine oxide group and trivalent nitrogen atom of the spacer unit coordinated to the metal cation. Following comparative compounds are referred to:

C1
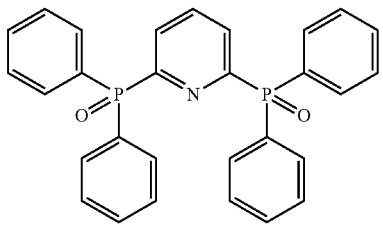

C2
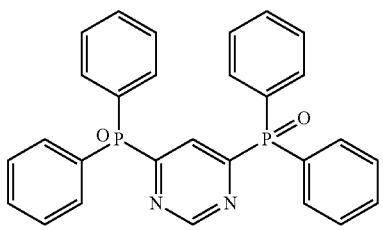

C3
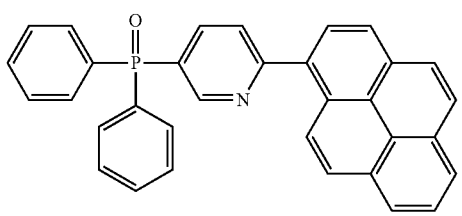

C4
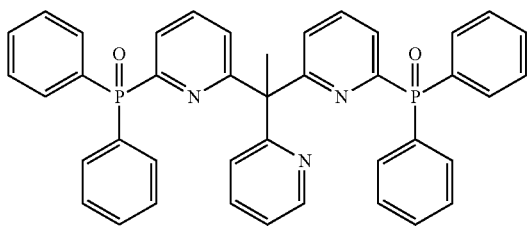

C5
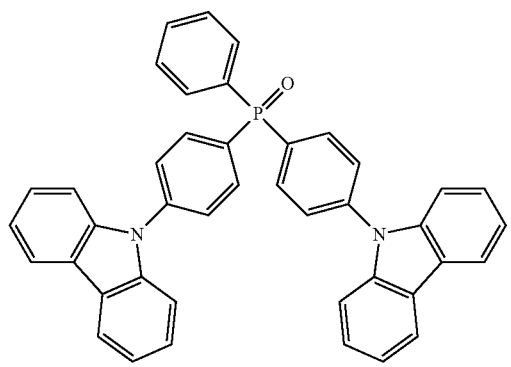

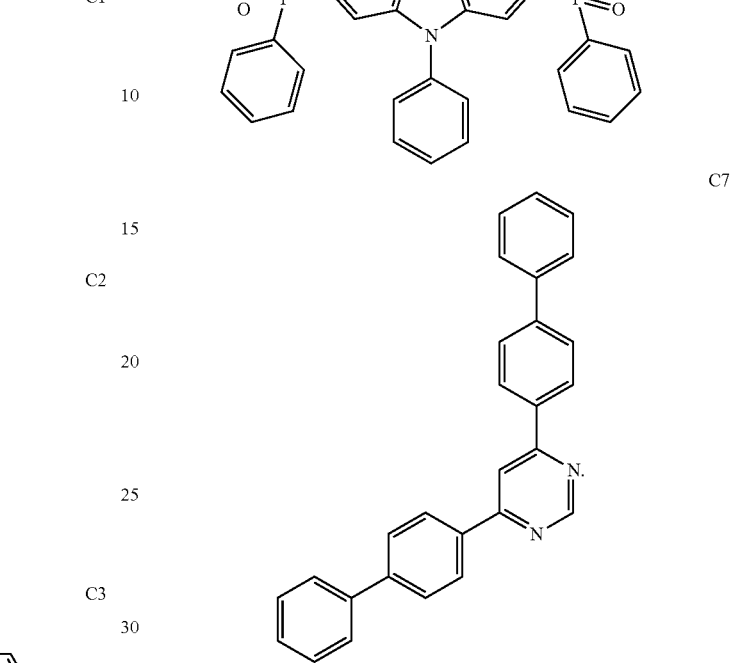

Table 1 shows inferior performance of C1, C2 and C4 in devices described in detail in the examples, which comprise the chelating unit including the PO group but lack the electron transporting unit E. Compound C3 isomeric with A2 and differing only in the feature that its nitrogen is not sterically available for chelate formation performs substantially worse than A2. Similarly, compounds C5 and C6, wherein the sterical arrangement of nitrogen atoms prevents chelate formation with metal cation which could include oxygen atom of the phosphine oxide group, have poor performance. Comparison of the compound C7 with compounds B1-B6 shows again the importance of the phosphine oxide group participation on the chelate formation.

TABLE 1

| Code | $E_{1/2}$ vs. $Fc^+/Fc$ (V) | D1 doped U (V) | D1 doped $Q_{eff}$ (%) | D2 doped U (V) | D2 doped $Q_{eff}$ (%) | D3 doped U (V) | D3 doped $Q_{eff}$ (%) |
|---|---|---|---|---|---|---|---|
| A1 | −2.33 | 5.2 | 4.1 | 4.9 | 5.4 | 4.1 | 5.1 |
| A2 | −2.34 | 4.7 | 5.4 | 4.6 | 6.8 | 4.1 | 6.5 |
| A3 | −2.27 | 5.1 | 5.9 | 4.7 | 6.1 | 4.2 | 6.2 |
| A4 | −2.33 | 5.0 | 5.4 | 4.4 | 6.3 | 3.8 | 6.9 |
| B1 | −2.06 | 6.5 | 2.3 | — | — | — | — |
| B2 | −2.20 | — | — | — | — | 5.0 | 6.0 |
| B3 | −2.20 | — | — | — | — | — | — |
| B4 | −2.26 | 6.6 | 3.8 | 6.4 | 5.1 | 5.9 | 5.9 |
| B5 | −2.10 | 5.5 | 3.3 | 5.5 | 3.1 | 5.1 | 4.2 |
| B6 | −2.09 | 5.1 | 4.0 | 5.6 | 4.0 | 4.7 | 4.8 |
| C1 | −2.52 | 6.4 | 3.1 | 6.5 | 5.0 | — | — |
| C2 | −1.91 | >10.0 | <1.0 | — | — | — | — |
| C3 | −2.24 | 5.4 | 4.1 | 5.3 | 5.3 | 4.6 | 6.5 |
| C4 | −2.21 | 5.7 | 4.2 | 6.7 | 4.1 | 7.6 | 4.1 |
| C5 | −2.86 | 7.3 | 2.7 | 7.5 | 3.9 | 7.8 | 2.6 |
| C6 | −2.51 | 5.8 | 3.5 | — | — | 5.0 | 5.4 |
| C7 | −2.29 | 6.2 | 3.8 | 6.9 | 3.8 | — | — |

EXAMPLES

General Remarks for Synthesis

All manipulations were carried out under argon in thoroughly dried glass vessels, without any further purification of commercial chemicals except for the use of dried and degassed solvents (solvent purification system (SPS) quality).

General Procedure A): Suzuki Couplings:

The halogen compound, the boronic acid, Pd(P$^t$Bu$_3$)$_4$ and the solvent (toluene or glyme) were mixed together, 2M aqueous K$_2$CO$_3$ solution was added. The mixture was stirred at 85° C. for 18 h. After cooling to room temperature the toluene phase was washed with water two times. Then, then organic phase was dried over MgSO$_4$ and reduced to dryness. The crude product was purified by column chromatography (SiO$_2$), General Procedure B): Phosphination by Aromatic Nucleophilic Substitution:

The halogen compound was solved in tetrahydrofurane (THF) at room temperature. Within 90 min 0.5M potassium diphenyl phosphide in THF solution was added. After one hour of stirring all solvents were removed and the residue was dissolved in dichloromethane (DCM). 30 wt. % aqueous solution of hydrogen peroxide was added slowly. The mixture was stirred over night. The organic phase was separated and the aqueous one extracted with DCM two times. Combining the organic phases, drying over MgSO$_4$ and removing the solvents provided a crude product, which was purified by column chromatography (SiO$_2$).

General Procedure C): Nucleophilic Arylation:

The halogen compound was solved in diethylether at 0° C. 2.5M n-BuLi solution in hexane was dropped to the solution within 15 min. The mixture was stirred at room temperature for 30 min and then cooled down to −30° C. 2-chloropyrimidine dissolved in THF was added within 15 min. The mixture was stirred at −30° C. for additional 45 min and then 60 min at 0° C. A mixture of acetic acid, water and THF was added. 10 min later 2,3-dichloro-5,6-dicyano-1,4-benzoquinone (DDQ) dissolved in THF was added. After the next 10 min a 3M aqueous solution of NaOH was added at room temperature. The reaction mixture was diluted with DCM and water. The organic phase was separated and the aqueous one extracted with DCM two times. Drying the organic phase over MgSO$_4$, reduction to dryness and finally purification by column chromatography (SiO$_2$) afforded the desired product.

General Procedure D): Phosphination & Oxidation:

The halogen compound was dissolved in THF at −80° C. 2.5M n-BuLi solution in hexane was dropped to the solution within 30 min. Stirring was continued for one hour. Diphenyl phosphine chloride was added slowly at −50° C. The reaction mixture was allowed to warm to room temperature and stirred over night. After addition of methanol and reduction to dryness, the residue was solved in DCM. 30 wt. % aqueous hydrogen peroxide was added and stirring was continued over night. The organic phase was separated and the aqueous one extracted with DCM three times. After drying the combined organic phases over MgSO$_4$ and reduction, the residue was purified by column chromatography to yield pure product.

Analytics:

Final materials were characterized by mass spectrometry and proton nuclear magnetic resonance ($^1$H-NMR). NMR samples were dissolved in CD$_2$Cl$_2$ unless otherwise stated. $^1$H-NMR spectra were taken at 500.13 MHz, and referenced to 5.31 ppm. Melting points were determined by differential scanning calorimetry (DSC). Peak temperatures are reported.

Pyridine Compounds (6-chloropyridin-2-yl)diphenylphosphine oxide

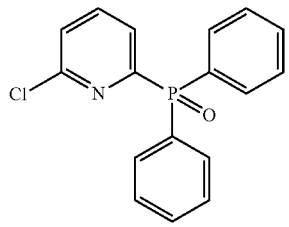 [SMILES: O=P(c1ccccc1)(c1ccccc1)c1cccc(Cl)n1]

Synthesis According to General Procedure B 2,6-dichloropyridine: 3.0 g (1.0 eq, 20.27 mmol)
0.5M potassium diphenyl phosphide in THF: 40.5 mL (1.0 eq, 20.27 mmol)
THF: 45 mL
DCM: 50 mL
30 wt. % aqueous H$_2$O$_2$: 15 mL
column chromatography (SiO$_2$, DCM: hexane 1:1)
Yield: 4.13 g (65%) white solid
Melting point: 103° C. (DSC, peak)
GC-MS: m/z=313

Diphenyl(6-(pyren-1-yl)pyridin-2-yl)phosphine oxide (A1)

Figure 3:
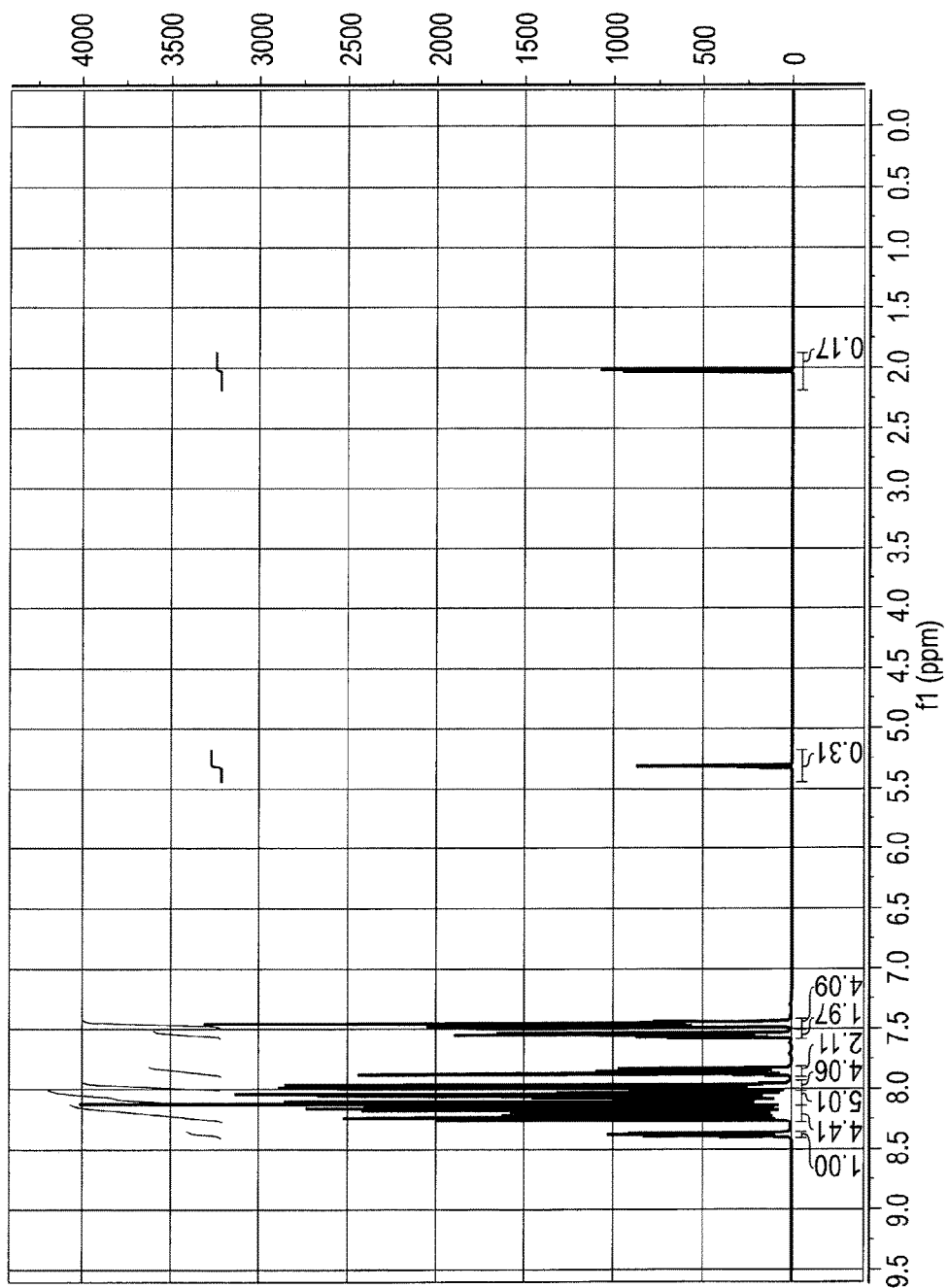
FIG. 3 shows $^1$H NMR spectrum of the inventive compound A1

Synthesis According to General Procedure A (6-chloropyridin-2-yl)diphenylphosphine oxide: 1.50 g (1.0 eq, 4.78 mmol)
1-pyreneboronic acid: 1.41 g (1.2 eq, 5.73 mmol)
Tetrakis(triphenylphosphine)palladium(0): 166 mg (3 mol. %, 0.14 mmol)
2M K$_2$CO$_3$: 7 mL (2.7 eq)
Dimethoxyethane: 15 mL
column chromatography (SiO$_2$, DCM, R$_f$=0.60)
Yield: 1.38 g (60%) yellow solid
Melting point: 224° C.
ESI-MS: m/z=502 (M+Na$^+$)
$^1$H-NMR: see FIG. 3

2-fluoro-5-(pyren-1-yl)pyridine

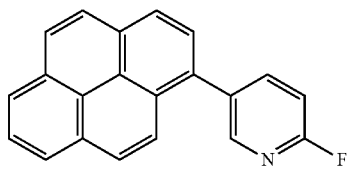 [SMILES: Fc1ccc(-c2ccc3ccc4cccc5ccc2c3c45)cn1]

Synthesis According to General Procedure A 5-bromo-2-fluoropyridine: 6.50 g (1.0 eq, 36.94 mmol)
1-pyreneboronic acid: 10.00 g (1.1 eq, 40.64 mmol)

Tetrakis(triphenylphosphine)palladium(0): 1.28 g (3 mol. %, 1.1 mmol)
2M $K_2CO_3$: 73 mL (4 eq)
toluene: 300 mL
column chromatography ($SiO_2$, DCM, $R_f$=0.60)
Yield: 8.8 g (80%)
Melting point: 114° C.
GC-MS: m/z=297 diphenyl(5-(pyren-1-yl)pyridin-2-yl)phosphine oxide (A2)

Figure 4:
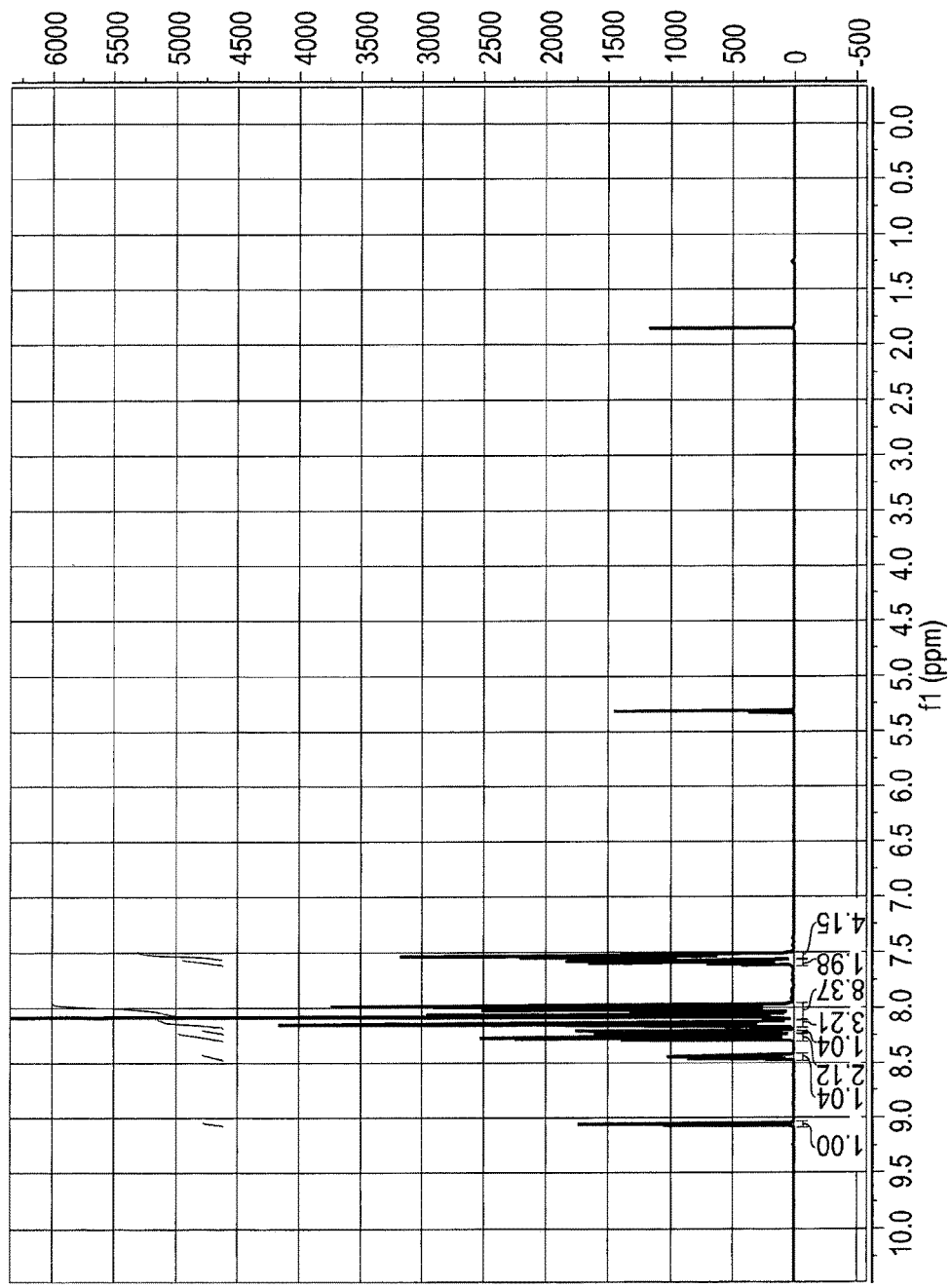
FIG. 4 shows $^1$H NMR spectrum of the inventive compound A2

Synthesis According to General Procedure B 2-fluoro-5-(pyren-1-yl)pyridine: 8.60 g (1.0 eq, 28.92 mmol)
0.5M potassiumdiphenylphosphide in THF: 58 mL (1.0 eq, 28.92 mmol)
THF: 500 mL
DCM: 50 mL
30 wt. % aqueous $H_2O_2$: 15 mL
column chromatography ($SiO_2$, EE, $R_f$=0.35)
Yield: 8.8 g (80%) yellow solid
Melting point: 207° C.
EI-MS: m/z=479
$^1$H-NMR: see FIG. 4

2-chloro-4-(pyren-1-yl)pyridine

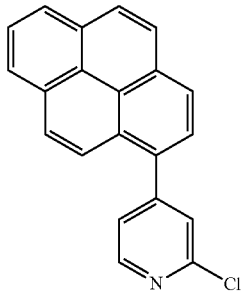 [SMILES: Clc1cc(-c2ccc3ccc4cccc5ccc2c3c45)ccn1]

Synthesis According to General Procedure A 4-bromo-2-chloropyridine: 7.10 g (1.0 eq, 36.94 mmol)
1-pyreneboronic acid: 10.00 g (1.1 eq, 40.64 mmol)
Tetrakis(triphenylphosphine)palladium(0): 1.28 g (3 mol. %, 1.1 mmol)
2M $K_2CO_3$: 73 mL (4 eq)
toluene: 300 mL
column chromatography ($SiO_2$, DCM, $R_f$=0.38)
Yield: 8.1 g (69%)
Melting point: 150° C.
GC-MS: m/z=313 diphenyl(4-(pyren-1-yl)pyridin-2-yl)phosphine oxide (A3)

Figure 5:
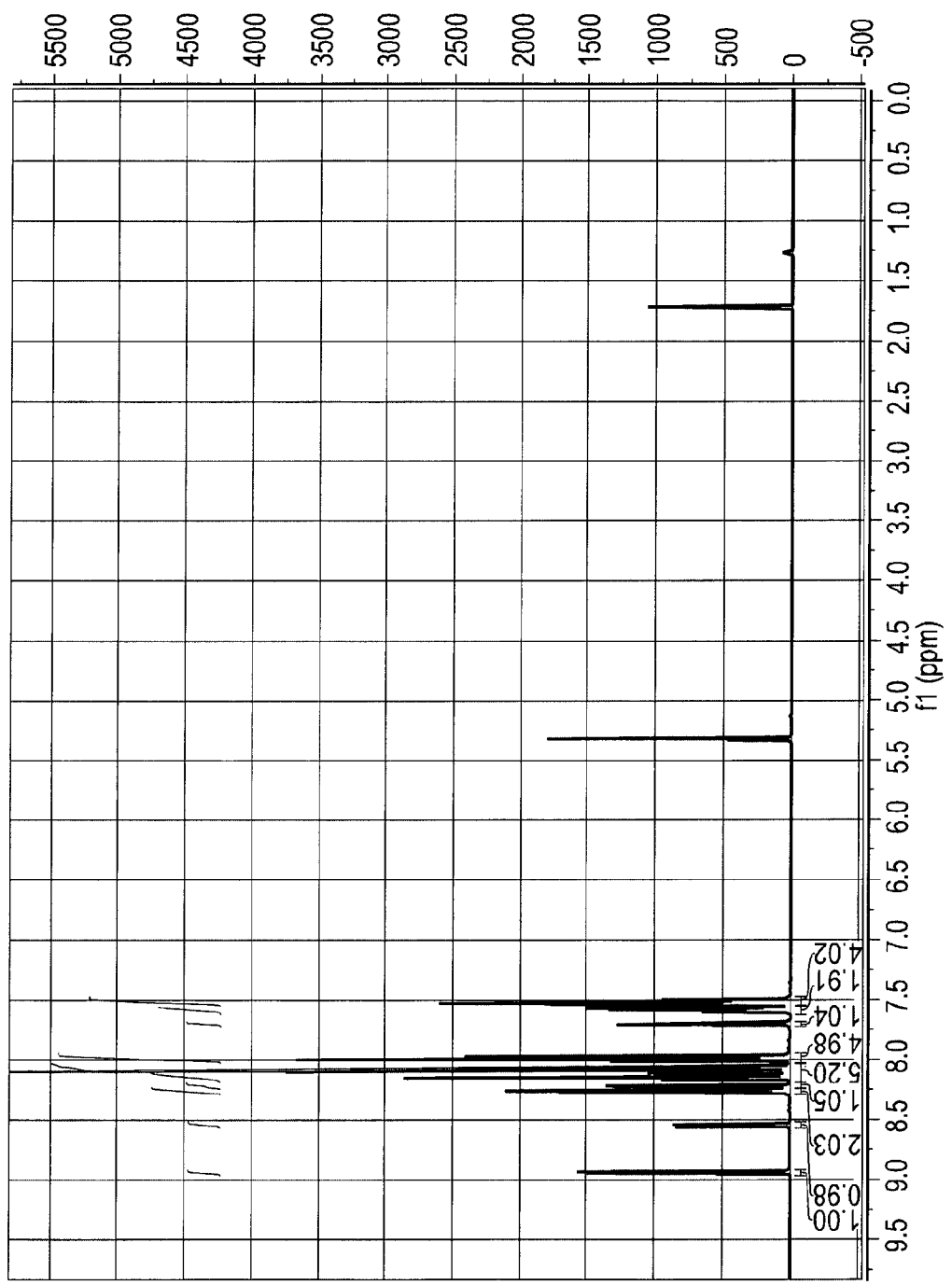
FIG. 5 shows $^1$H NMR spectrum of the inventive compound A3

Synthesis According to General Procedure B 2-chloro-4-(pyren-1-yl)pyridine: 7.80 g (1.0 eq, 24.86 mmol)
0.5M potassium diphenylphosphide in THF: 47.7 mL (1.0 eq, 24.86 mmol)
THF: 450 mL
DCM: 50 mL
30 wt. % aqueous $H_2O_2$: 15 mL
column chromatography ($SiO_2$, DCM)
Yield: 8.2 g (69%) pale yellow solid
Melting point: 244° C.
EI-MS: m/z=479
$^1$H-NMR: see FIG. 5 bis(6-bromopyridin-2-yl)(phenyl)phosphine oxide

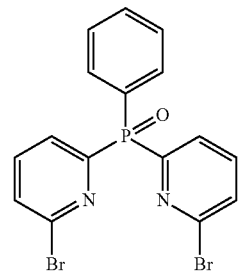 [SMILES: O=P(c1ccccc1)(c1cccc(Br)n1)c1cccc(Br)n1]

2,6-dibromopyridine (5.0 g, 1.0 eq, 21.11 mmol) was dissolved in diethylether (50 mL) and cooled to −80° C. 1.6M BuLi solution in hexane (8.4 mL, 1.0 eq, 21.11 mL) was added dropwise. The solution was stirred for 30 min and dichlorophenylphosphine (1.89 g, 0.5 eq, 10.56 mmol) was added slowly afterwards. The solution was allowed to warm to room temperature and was stirred over night. The mixture was quenched by 2M aqueous HCl (100 mL). The phases were separated and the aqueous one extracted with DCM two times. The combined organic phases were dried over $MgSO_4$ and reduced to dryness. The residue was solved in DCM (100 mL) and oxidized with 30% aqueous hydrogenperoxide solution (20 mL). 16 h later, water was added and the mixture was extracted with DCM two times. The combined organic phases were dried over $MgSO_4$ and reduced to dryness. Finally the crude product was purified by column chromatography ($SiO_2$, ethyl acetate (EE)).

Yield: 1.93 g (42%) white solid.

phenylbis(6-(pyren-1-yl)pyridin-2-yl)phosphine oxide (A4)

Figure 6:
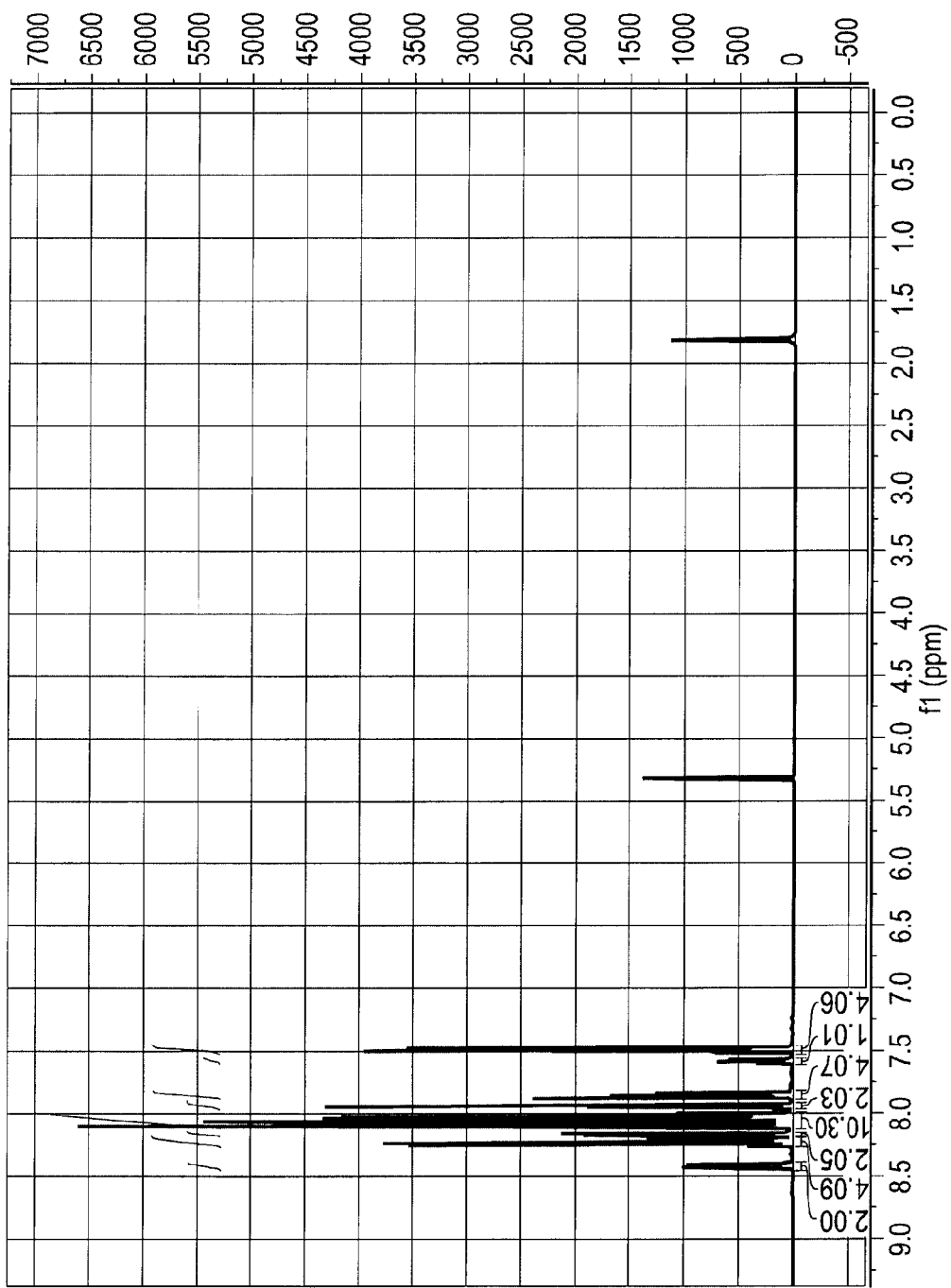
FIG. 6 shows $^1$H NMR spectrum of the inventive compound A4

Synthesis According to General Procedure A bis(6-bromopyridin-2-yl)(phenyl)phosphine oxide: 5.60 g (1.0 eq, 12.78 mmol)
1-pyreneboronic acid: 7.86 g (2.5 eq, 31.96 mmol)
Tetrakis(triphenylphosphine)palladium(0): 886 mg (6 mol %, 0.77 mmol)
2M $K_2CO_3$: 55 mL (8 eq)
toluene: 100 mL
column chromatography ($SiO_2$, EE:MeOH 10:1)
Yield: 3.4 g (39%) pale yellow solid
ESI-MS: m/z=703 (M+Na$^+$)
$^1$H-NMR: see FIG. 6

(9,10-di(naphthalen-2-yl)anthracen-2-yl)boronic acid

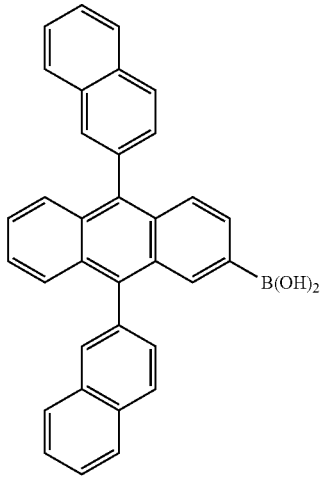 [SMILES: OB(O)c1ccc2c(-c3ccc4ccccc4c3)c3ccccc3c(-c3ccc4ccccc4c3)c2c1]

2-bromo-9,10-di(naphthalen-2-yl)anthracene (10.00 g, 1.0 eq, 19.63 mmol) was dissolved in THF (140 mL) and cooled to −78° C. At this temperature n-BuLi (2.5M in hexane, 10.2 mL, 1.3 eq, 25.52 mmol) was added dropwise and the mixture was stirred for 2 hours. Afterwards, B(OMe)$_3$ (6.12 g, 3.0 eq, 58.89 mmol) was added at −78° C. and the reaction mixture was allowed to warm up to room temperature. After stirring for 17 hours the mixture was quenched with HCl, the yellow precipitate was filtered off and washed with water (2×30 mL). The residue was dried in vacuo and used without further purification.

Yield: 9.8 g (yield 100%)

5-(9,10-di(naphthalen-2-yl)anthracen-2-yl)-2-fluoropyridine

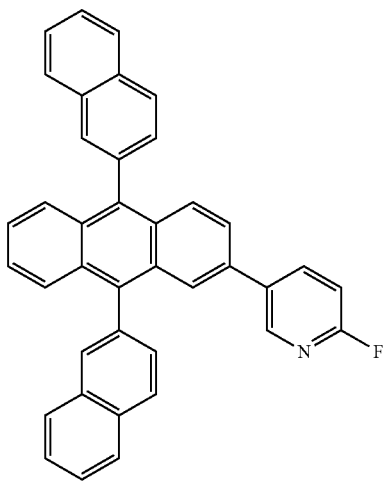 [SMILES: Fc1ccc(-c2ccc3c(-c4ccc5ccccc5c4)c4ccccc4c(-c4ccc5ccccc5c4)c3c2)cn1]

Synthesis According to General Procedure A 5-bromo-2-fluoropyridine: 1.33 g (1.2 eq, 7.58 mmol)
(9,10-di(naphthalen-2-yl)anthracen-2-yl)boronic acid: 3.00 g (1.0 eq, 6.32 mmol)

Tetrakis(triphenylphosphine)palladium(0): 219 mg (3 mol. %, 0.19 mmol)
2M K$_2$CO$_3$: 6.5 mL (4 eq)
DME: 20 mL
No column chromatography needed, precipitated during work up as yellow solid
Yield: 1.7 g (51%)
ESI-MS: m/z=526 (M+H$^+$)

(5-(9,10-di(naphthalen-2-yl)anthracen-2-yl)pyridin-2-yl)diphenylphosphine oxide (A5)

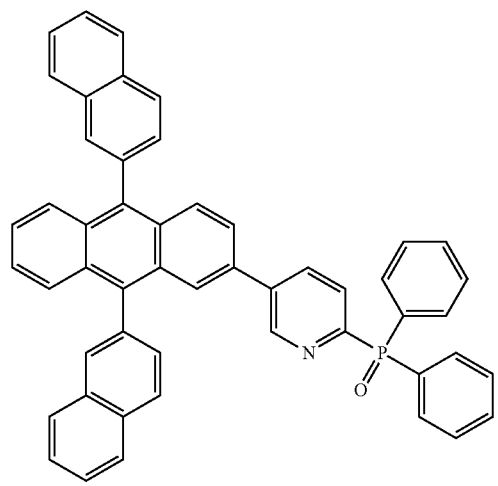 [SMILES: O=P(c1ccccc1)(c1ccccc1)c1ccc(-c2ccc3c(-c4ccc5ccccc5c4)c4ccccc4c(-c4ccc5ccccc5c4)c3c2)cn1]

Figure 7:
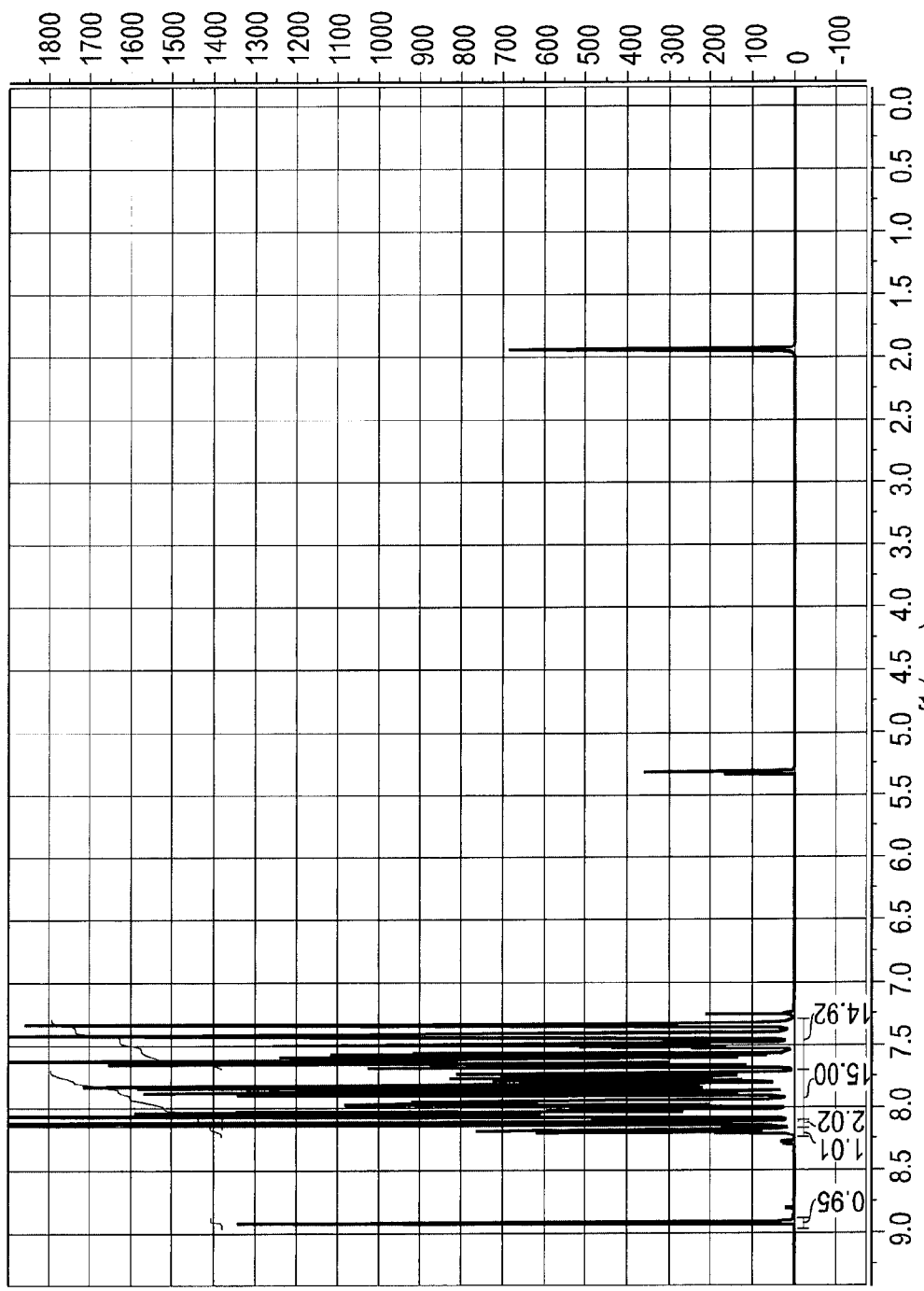
FIG. 7 shows $^1$H NMR spectrum of the inventive compound A5

Synthesis According to General Procedure B 5-(9,10-di(naphthalen-2-yl)anthracen-2-yl)-2-fluoropyridine: 2.89 g (1.0 eq, 5.45 mmol)
0.5M potassiumdiphenylphosphide in THF: 11.5 mL (1.05 eq, 5.8 mmol)
THF: 170 mL
DCM: 50 mL
30 wt. % aqueous H$_2$O$_2$: 10 mL
column chromatography (SiO$_2$, DCM:MeOH 40:1, R$_f$=0.66)
Yield: 2.99 g (76%)
ESI-MS: m/z=730 (M+Na$^+$)
$^1$H-NMR: see FIG. 7 bis(5-chloropyridin-2-yl)(phenyl)phosphine oxide

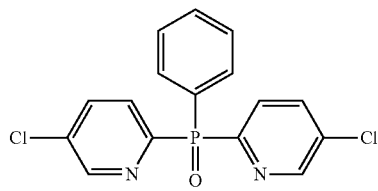 [SMILES: O=P(c1ccccc1)(c1ccc(Cl)cn1)c1ccc(Cl)cn1]

2-bromo-5-chloropyridine (3.0 g, 1.0 eq, 15.6 mmol) was dissolved in THF (20 mL). 2.0M $^i$PrMgCl solution in THF (7.8 mL, 15.6 mmol) was added slowly. The solution was stirred for 3 h and cooled to −78° C. afterwards. Dichlorophenylphosphine (1.395 g, 7.79 mmol) was added slowly.

After warming to room temperature, the solution was stirred over night. The reaction was stopped with some amounts of methanol and all solvents were removed afterwards. The residue was dissolved in DCM (60 mL) and 30 wt. % aqueous hydrogenpeoxide solution (6 mL) was added. The solution was stirred over night. The organic phase was separated, washed with water, dried over $MgSO_4$ and reduced to dryness. The crude product was purified by column chromatography ($SiO_2$, EE, $R_f$=0.35)

Yield: 0.96 g (35%)
EI-MS: M/Z=348/350 phenylbis(5-(pyren-1-yl)pyridin-2-yl)phosphine oxide (A6)

Synthesis According to General Procedure A bis(5-chloropyridin-2-yl)(phenyl)phosphine oxide: 0.9 g (1.0 eq, 2.58 mmol)
1-pyreneboronic acid: 1.39 g (2.2 eq, 5.67 mmol)
Tetrakis(triphenylphosphine)palladium(0): 120 mg (3 mol %, 0.10 mmol)
2M $K_2CO_3$: 10 mL (4 eq)
Glyme: 12 mL
column chromatography ($SiO_2$, EE:DCM 9:1, $R_f$=0.23)
Yield: 1.28 g (73%)
ESI-MS: m/z=681 (M+H$^+$)

Pyrimidine Compounds 2-chloro-4-(pyren-1-yl)pyrimidine

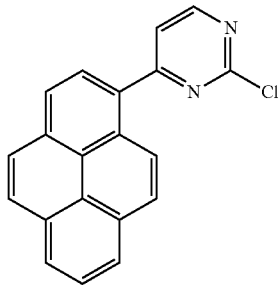 [SMILES: Clc1nccc(-c2ccc3ccc4cccc5ccc2c3c45)n1]

Synthesis According to General Procedure C 1-bromopyrene: 2.0 g (1.1 eq, 7.1 mmol)
Ether: 75 mL
2.5M n-BuLi in hexane: 2.8 mL (1.1 eq, 7.1 mmol)
2-chloropyrimidine: 0.74 g (1.0 eq, 6.5 mmol)
THF: 30 mL
Acetic acid/water/THF: 427 mg (1.1 eq, 7.1 mmol)/116 mg (1.0 eq)/5 mL
DDQ: 1.61 g (1.1 eq, 7.1 mmol)
3M aqueous NaOH: 3.2 mL (1.5 eq)
Column chromatography ($SiO_2$, EE:hexane 1:1, $R_f$=0.65)
Yield: 1.4 g (71%)
Melting point: 181° C.
GC-MS: m/z=266 diphenyl(4-(pyren-1-yl)pyrimidin-2-yl)phosphine oxide (B1)

Figure 8:
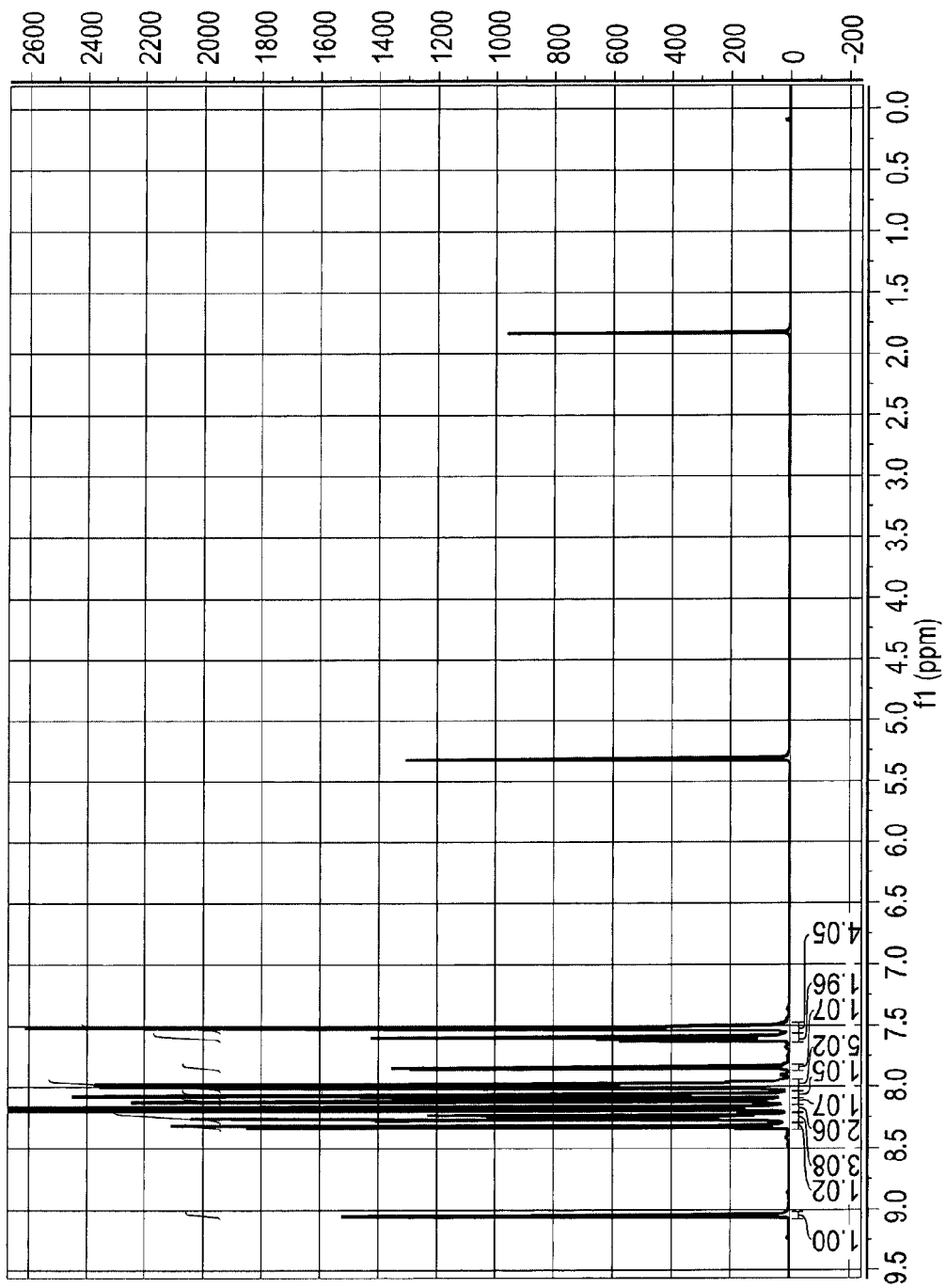
FIG. 8 shows $^1$H NMR spectrum of the inventive compound B1

Synthesis According to General Procedure B 2-chloro-4-(pyren-1-yl)pyrimidine: 1.20 g (1.15 eq, 3.81 mmol)
0.5M potassiumdiphenylphosphide in THF: 6.6 mL (1.0 eq, 3.31 mmol)
THF: 12 mL
DCM: 60 mL
30 wt. % aqueous $H_2O_2$: 2 mL
column chromatography ($SiO_2$, EE, $R_f$=0.10)
Yield: 1.1 g (70%)
Melting point: 233° C.
EI-MS: m/z=480
$^1$H-NMR: see FIG. 8

2-chloro-5-(pyren-1-yl)pyrimidine

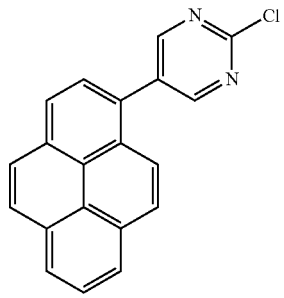 [SMILES: Clc1ncc(-c2ccc3ccc4cccc5ccc2c3c45)cn1]

Synthesis According to General Procedure A 5-bromo-2-chloropyrimidine: 2.36 g (1.0 eq, 12.2 mmol)
1-pyreneboronic acid: 3.0 g (1.0 eq, 12.2 mmol)
Tetrakis(triphenylphosphine)palladium(0): 423 mg (3 mol. %, 0.4 mmol)
2M $K_2CO_3$: 25 mL (4 eq)
toluene: 1250 mL
column chromatography ($SiO_2$, hexane:EE, $R_f$=0.46)
Yield: 2.2 g (57%)
Melting point: 214° C.
GC-MS: m/z=314 diphenyl(5-(pyren-1-yl)pyrimidin-2-yl)phosphine oxide (B2)

Figure 9:
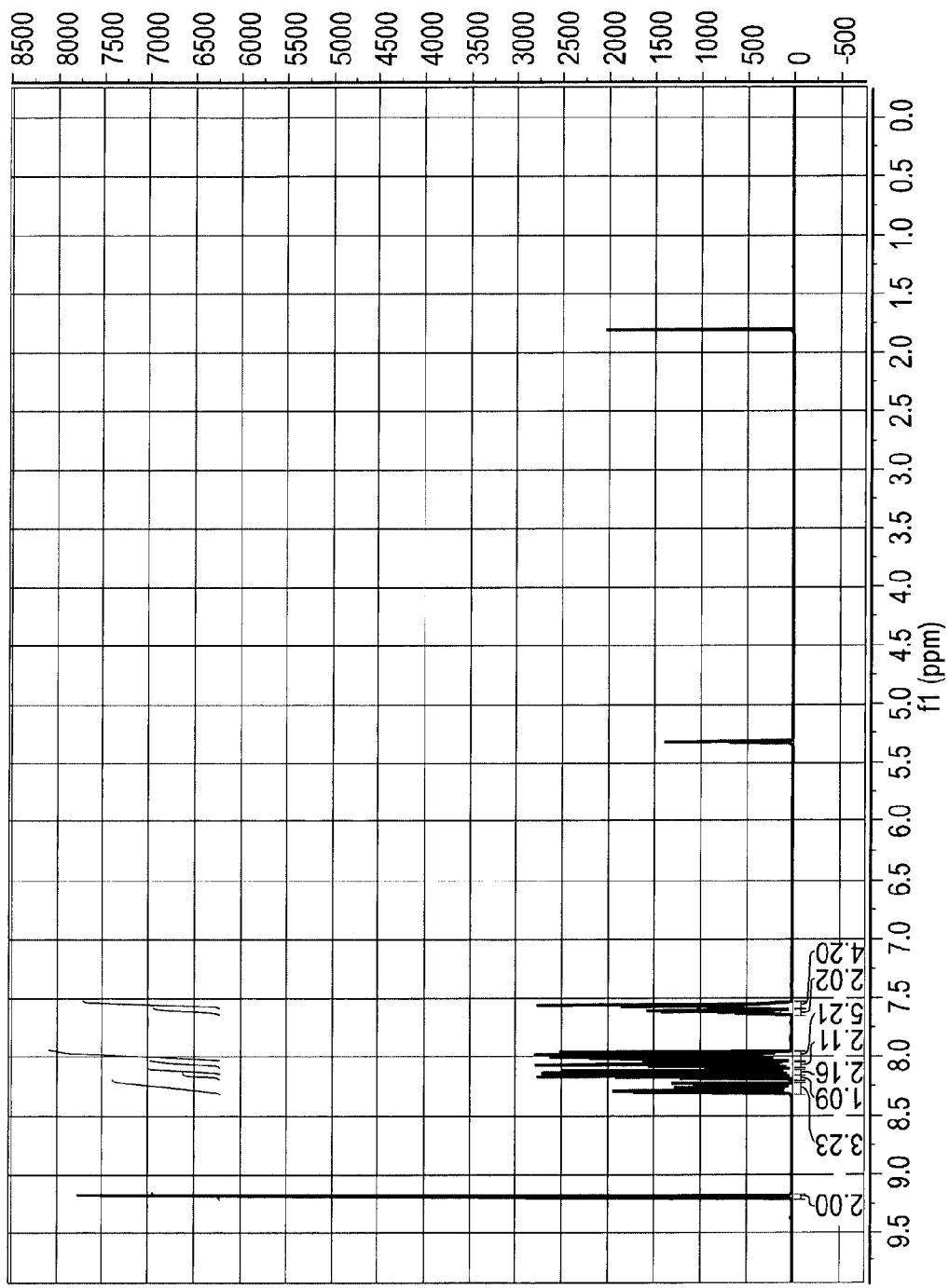
FIG. 9 shows $^1$H NMR spectrum of the inventive compound B2

Synthesis According to General Procedure B 2-chloro-5-(pyren-1-yl)pyrimidine: 2.00 g (1.0 eq, 6.35 mmol)
0.5M potassiumdiphenylphosphide in THF: 12.7 mL (1.0 eq, 6.35 mmol)
THF: 120 mL
DCM: 40 mL
30 wt. % aqueous $H_2O_2$: 5 mL
column chromatography ($SiO_2$, EE, $R_f$=0.18)
Yield: 2.1 g (70%)
Melting point: 220° C.
EI-MS: m/z=480
$^1$H-NMR: see FIG. 9

4-([1,1'-biphenyl]-4-yl)-2-chloropyrimidine

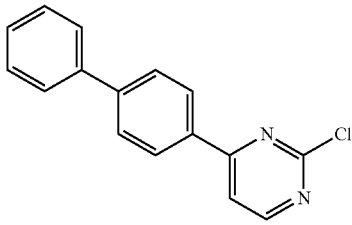 [SMILES: Clc1nccc(-c2ccc(-c3ccccc3)cc2)n1]

Synthesis According to General Procedure C 4-bromobiphenyl: 6.72 g (1.1 eq, 28.8 mmol)
Ether: 200 mL
2.5M n-BuLi in hexane: 11.5 mL (1.1 eq, 28.8 mmol)
2-chloropyrimidine: 3.0 g (1.0 eq, 26.2 mmol)
THF: 70 mL
Acetic acid/water/THF: 1.73 g (1.1 eq, 28.8 mmol)/0.48 mL (1.0 eq)/10 mL
DDQ: 6.54 g (1.1 eq, 28.8 mmol)
3M aqueous NaOH: 13 mL (1.5 eq)
column chromatography ($SiO_2$, EE:hexane 2:3)
Yield: 5.5 g (79%)
Melting point: 187° C.
GC-MS: m/z=266

(4-([1,1'-biphenyl]-4-yl)pyrimidin-2-yl)diphenylphosphine oxide (B3)

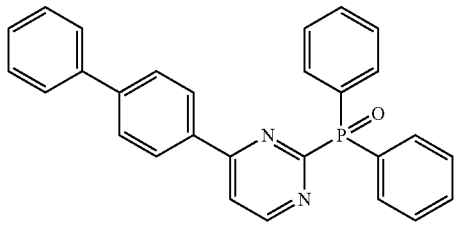 [SMILES: O=P(c1ccccc1)(c1ccccc1)c1nccc(-c2ccc(-c3ccccc3)cc2)n1]

Figure 10:
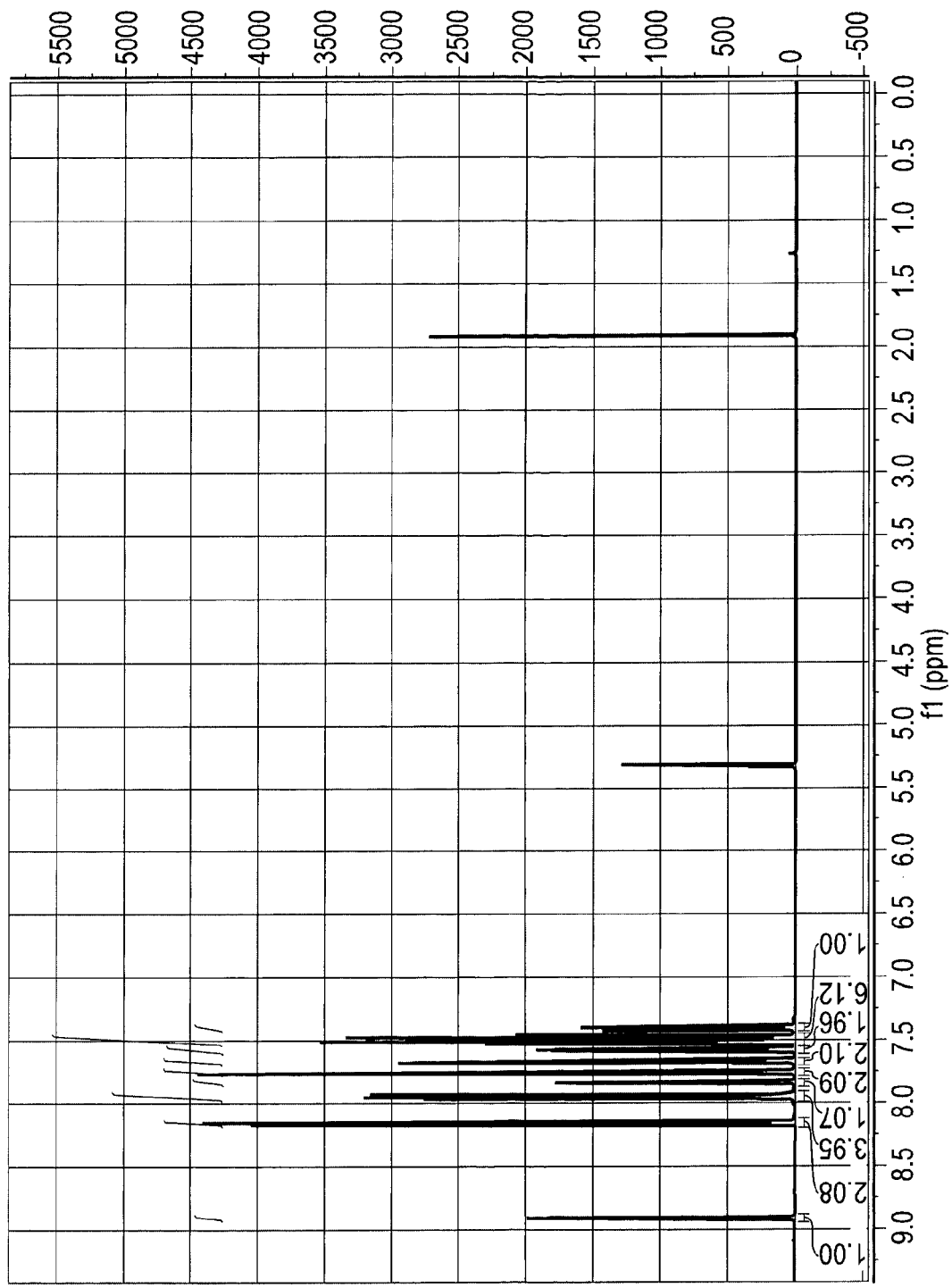
FIG. 10 shows $^1$H NMR spectrum of the inventive compound B3

Synthesis According to General Procedure B 4-([1,1'-biphenyl]-4-yl)-2-chloropyrimidine: 3.00 g (1.0 eq, 11.2 mmol)
0.5M potassiumdiphenylphosphide in THF: 22.5 mL (1.0 eq, 11.2 mmol)
THF: 200 mL
DCM: 50 mL
30 wt. % aqueous $H_2O_2$: 5 mL
column chromatography ($SiO_2$, EE, $R_f$=0.16)
Yield: 4.26 g (87%)
Melting point: 235° C.
EI-MS: m/z=432
$^1$H-NMR: FIG. 10

5-([1,1'-biphenyl]-4-yl)-2-chloropyrimidine

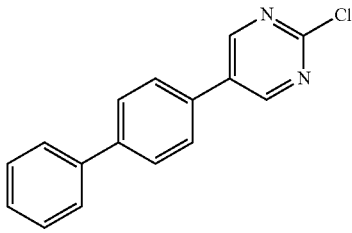 [SMILES: Clc1ncc(-c2ccc(-c3ccccc3)cc2)cn1]

Synthesis According to General Procedure A 5-bromo-2-chloropyrimidine: 2.93 g (1.0 eq, 15.15 mmol)
4-biphenylboronic acid: 3.0 g (1.0 eq, 15.15 mmol)
Tetrakis(triphenylphosphine)palladium(0): 0.53 g (3 mol. %, 0.45 mmol)
2M $K_2CO_3$: 30 mL (4 eq)
toluene: 140 mL
column chromatography ($SiO_2$, hexane:DCM 1:2, $R_f$=0.10)
Yield: 2.21 g (54%)
Melting point: 176° C.
GC-MS: m/z=266

(5-([1,1'-biphenyl]-4-yl)pyrimidin-2-yl)diphenylphosphine oxide (B4)

Figure 11:
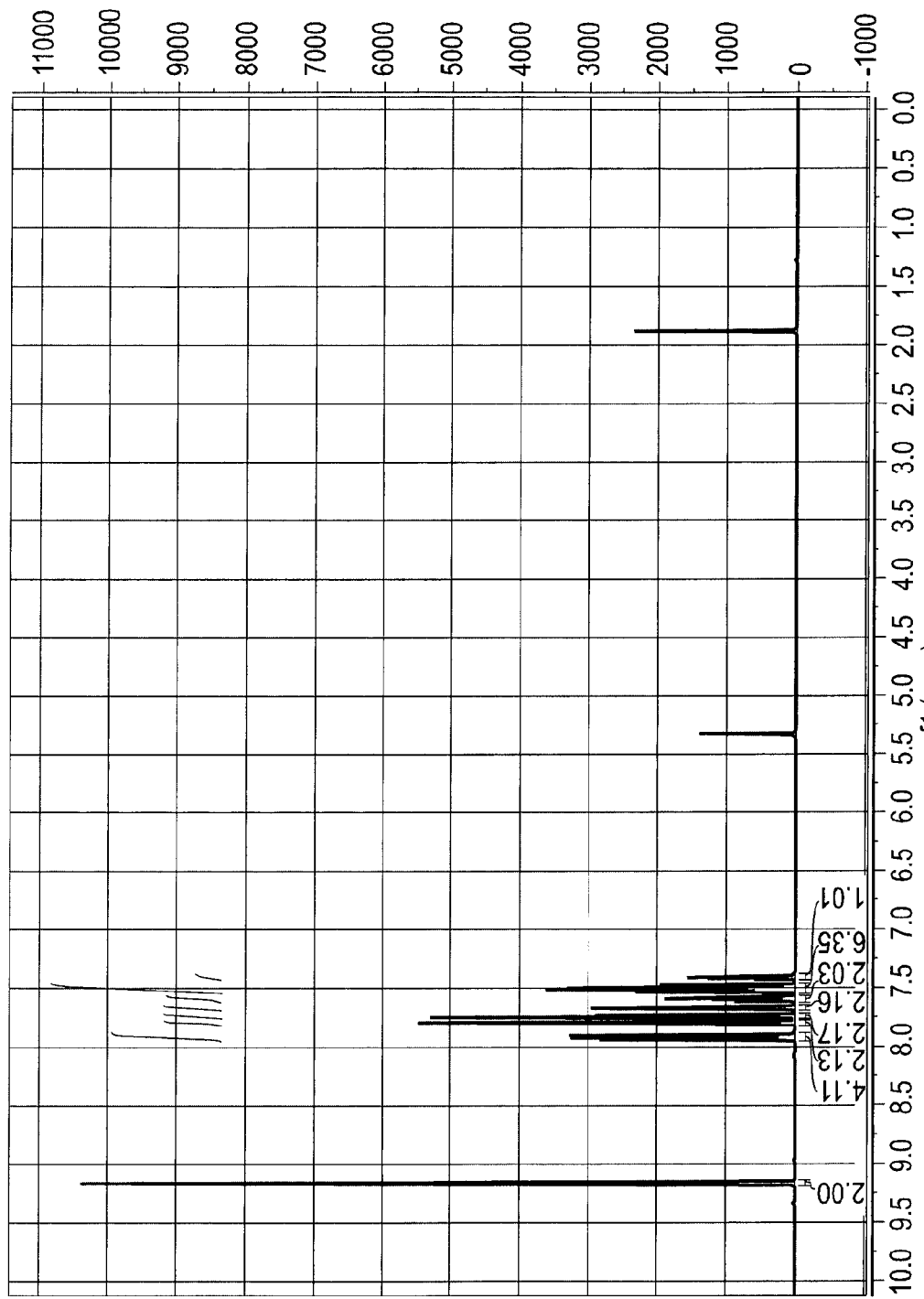
FIG. 11 shows $^1$H NMR spectrum of the inventive compound B4

Synthesis According to General Procedure B 5-([1,1'-biphenyl]-4-yl)-2-chloropyrimidine: 1.90 g (1.0 eq, 7.12 mmol)
0.5M potassiumdiphenylphosphide in THF: 14.3 mL (1.0 eq, 7.12 mmol)
THF: 120 mL
DCM: 50 mL
30 wt. % aqueous $H_2O_2$: 5 mL
column chromatography ($SiO_2$, EE, $R_f$=0.26)
Yield: 2.69 g (87%)
Melting point: 200° C.
EI-MS: m/z=432
$^1$H-NMR: see FIG. 11

4,6-di([1,1'-biphenyl]-4-yl)-2-chloropyrimidine

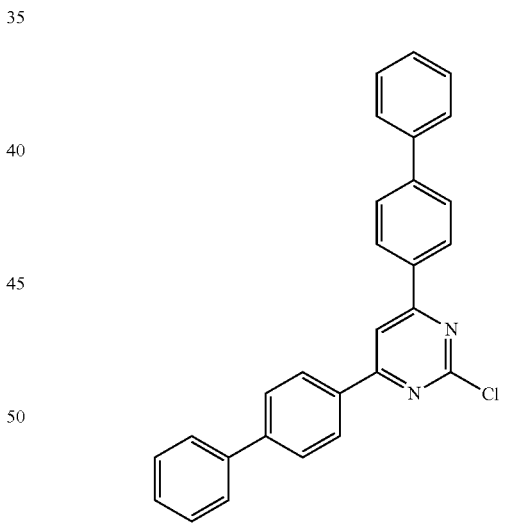

Synthesis According to General Procedure A 2,4,6-trichloropyrimidine: 3.0 g (1.0 eq, 16.4 mmol)
4-biphenylboronic acid: 6.48 g (2.0 eq, 32.7 mmol)
Tetrakis(triphenylphosphine)palladium(0): 756 mg (4 mol. %, 0.65 mmol)
2M $K_2CO_3$: 33 mL (4 eq)
glyme: 25 mL
column chromatography ($SiO_2$, DCM, $R_f$=0.77)
Yield: 1.12 g (16%)
GC-MS: m/z=418

(4,6-di([1,1'-biphenyl]-4-yl)pyrimidin-2-yl)diphenylphosphine oxide (B5)

Figure 12:
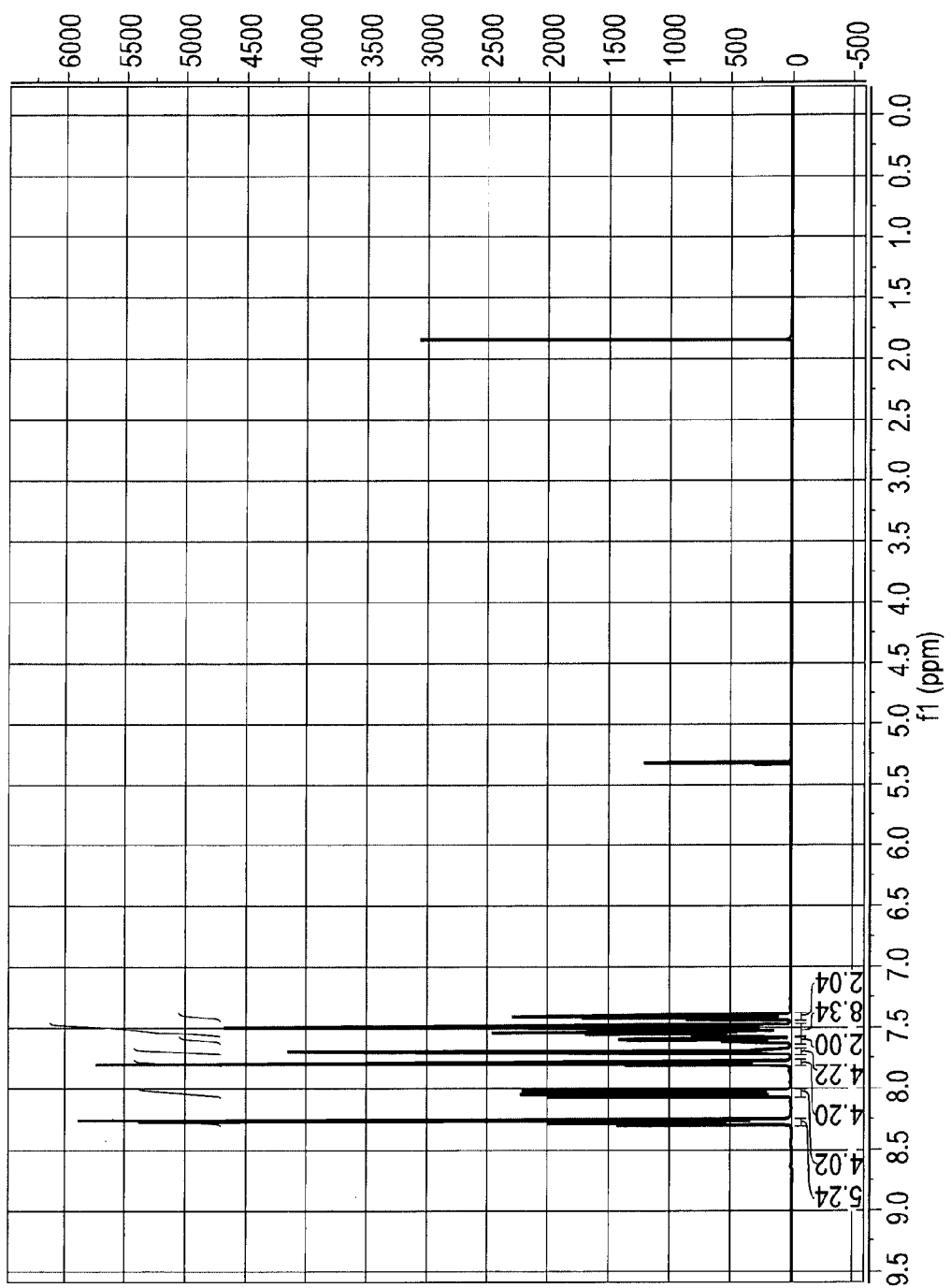
FIG. 12 shows $^1$H NMR spectrum of the inventive compound B5

Synthesis According to General Procedure B 4,6-di([1,1'-biphenyl]-4-yl)-2-chloropyrimidine: 1.12 g (1.0 eq, 2.67 mmol)
0.5M potassiumdiphenylphosphide in THF: 5.4 mL (1.0 eq, 2.67 mmol)
THF: 60 mL
DCM: 50 mL
30 wt. % aqueous $H_2O_2$: 15 mL
column chromatography ($SiO_2$, EE, $R_f$=0.68)
Yield: 1.34 g (86%)
Melting point: 239° C.
EI-MS: m/z=584
$^1$H-NMR: see FIG. 12

2-chloro-4,6-di(naphthalen-2-yl)pyrimidine

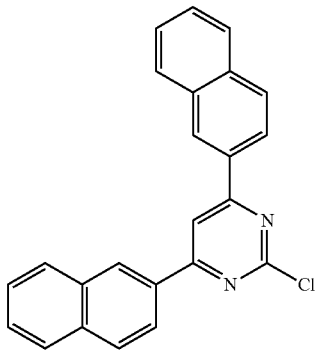 [SMILES: Clc1nc(-c2ccc3ccccc3c2)cc(-c2ccc3ccccc3c2)n1]

Synthesis According to General Procedure A 2,4,6-trichloropyrimidine: 3.0 g (1.0 eq, 16.4 mmol)
2-naphthylboronic acid: 5.63 g (2.0 eq, 32.7 mmol)
Tetrakis(triphenylphosphine)palladium(0): 756 mg (4 mol. %, 0.65 mmol)
2M $K_2CO_3$: 33 mL (4 eq)
glyme: 25 mL
column chromatography ($SiO_2$, DCM, $R_f$=0.77)
Yield: 2.81 g (46%)
GC-MS: m/z=366

(4,6-di(naphthalen-2-yl)pyrimidin-2-yl)diphenylphosphine oxide (B6)

Figure 13:
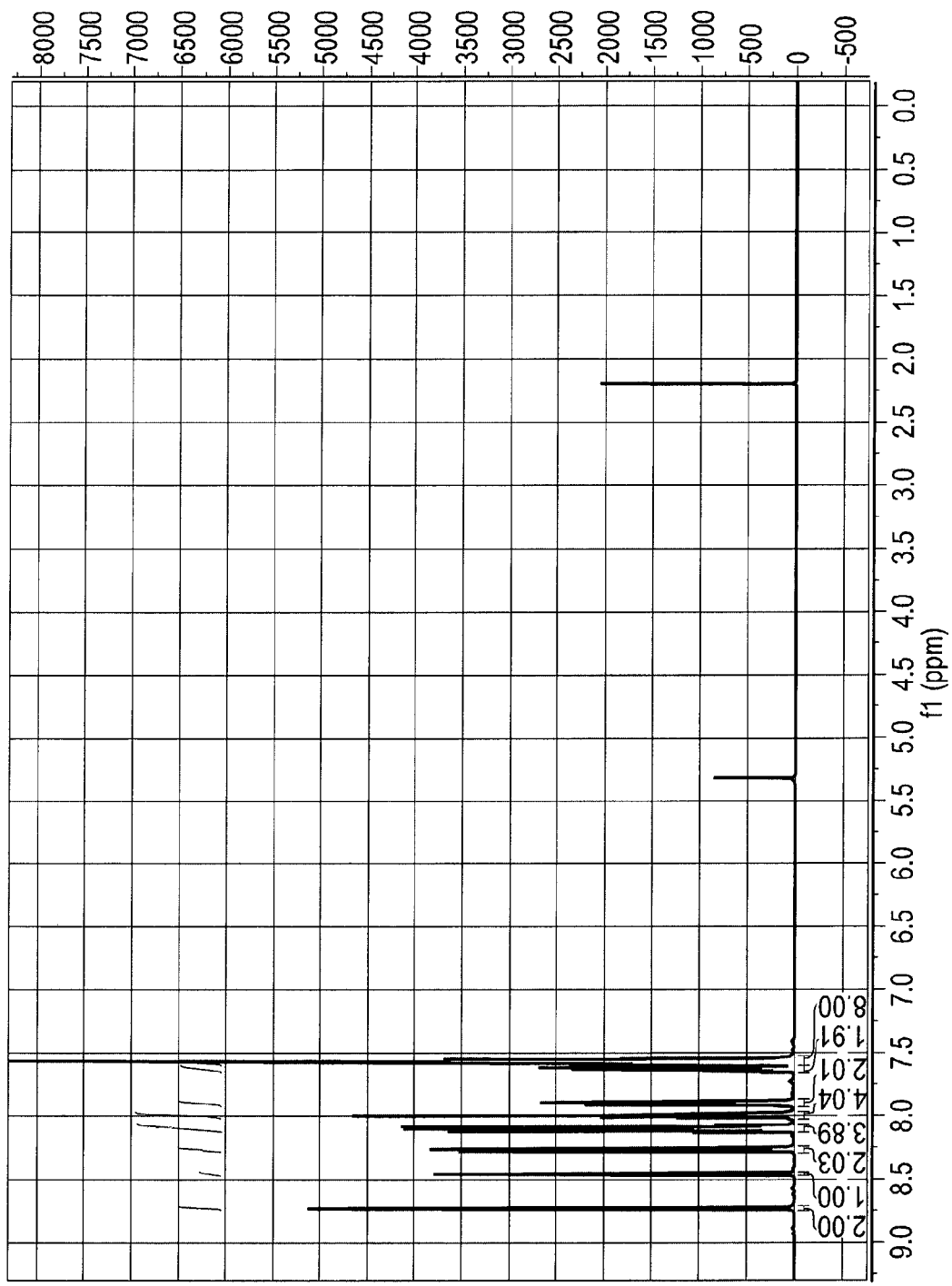
FIG. 13 shows $^1$H NMR spectrum of the inventive compound B6

Synthesis According to General Procedure B 2-chloro-4,6-di(naphthalen-2-yl)pyrimidine: 2.80 g (1.0 eq, 7.63 mmol)
0.5M potassiumdiphenylphosphide in THF: 15.3 mL (1.0 eq, 7.63 mmol)
THF: 150 mL
DCM: 60 mL
30 wt. % aqueous $H_2O_2$: 15 mL
column chromatography ($SiO_2$, EE, $R_f$=0.47)
Yield: 3.15 g (77%)
Melting point: 226° C.
EI-MS: m/z=532
$^1$H-NMR: see FIG. 13

Comparative Compounds pyridine-2,6-diylbis(diphenylphosphine oxide) (C1)

Figure 14:
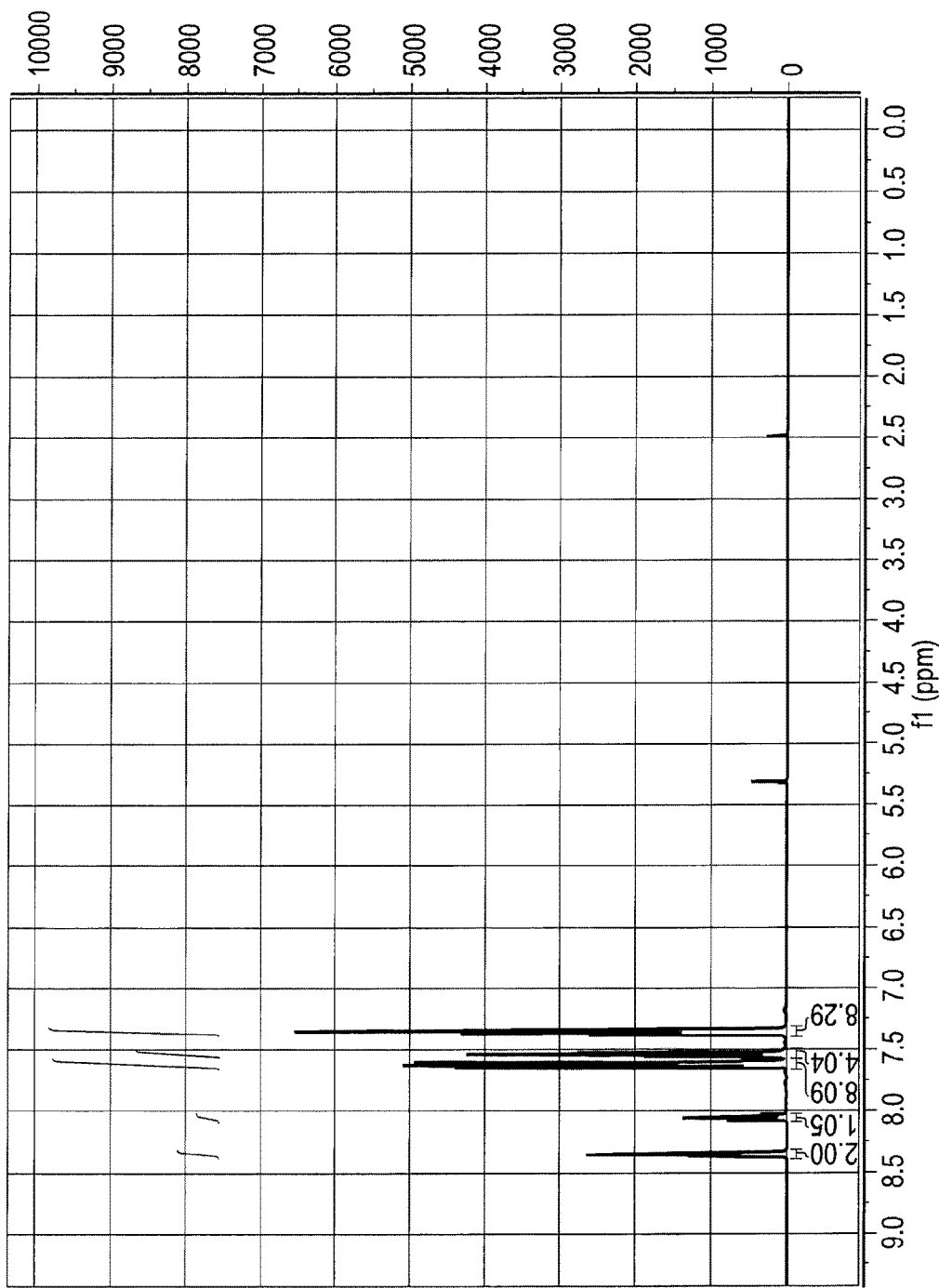
FIG. 14 shows $^1$H NMR spectrum of the comparative compound C1

Synthesis According to General Procedure B 2,6-difluoropyridine: 5.0 g (1.0 eq, 43.4 mmol)
0.5M potassiumdiphenylphosphide in THF: 82.6 mL (1.0 eq, 41.4 mmol)
THF: 150 mL
DCM: 50 mL
30 wt. % aqueous $H_2O_2$: 15 mL
column chromatography ($SiO_2$, EE, $R_f$=0.29)
Yield: 6.33 g (30%)
Melting point: 235° C.
EI-MS: m/z=479
$^1$H-NMR: see FIG. 14 pyrimidine-4,6-diylbis(diphenylphosphine oxide) (C2)

Figure 15:
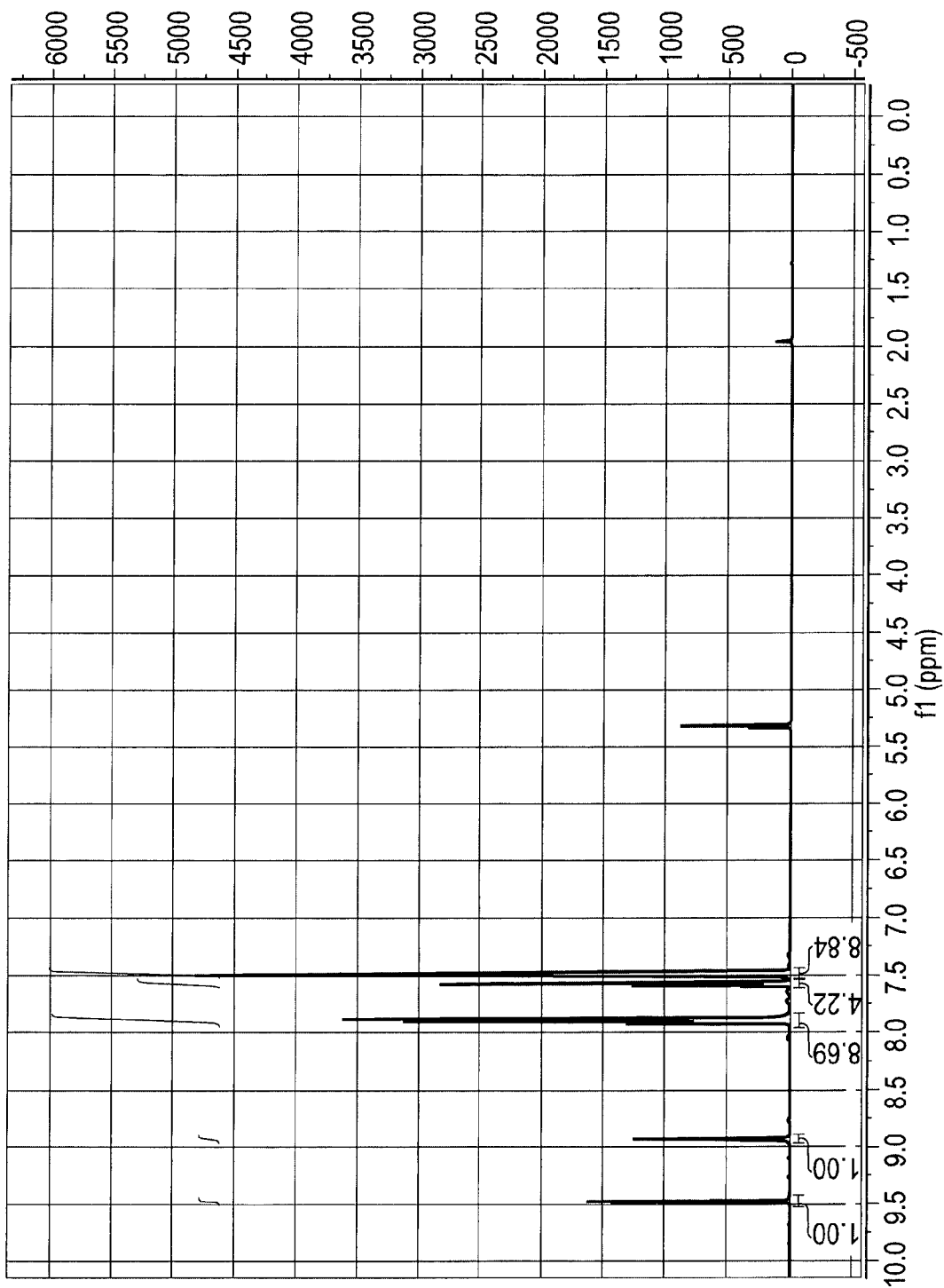
FIG. 15 shows $^1$H NMR spectrum of the comparative compound C2

Synthesis According to General Procedure B 4,6-dichloroyrimidine: 3.0 g (1.0 eq, 20.1 mmol)
0.5M potassiumdiphenylphosphide in THF: 40.1 mL (1.0 eq, 20.1 mmol)
THF: 50 mL
DCM: 60 mL
30 wt. % aqueous $H_2O_2$: 8 mL
column chromatography ($SiO_2$, EE, $R_f$=0.15)
Yield: 1.8 g (19%)
Melting point: 235° C.
EI-MS: m/z=480
$^1$H-NMR: see FIG. 15

5-fluro-2-(pyren-1-yl)pyridine

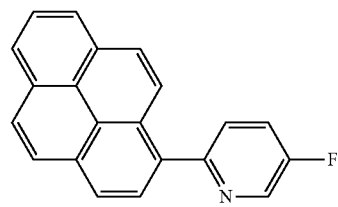 [SMILES: Fc1ccc(-c2ccc3ccc4cccc5ccc2c3c45)nc1]

Synthesis According to General Procedure A 2-bromo-5-fluoropyridine: 1.95 g (1.0 eq, 11.1 mmol)
1-pyreneboronic acid: 3.00 g (1.1 eq, 12.2 mmol)
Tetrakis(triphenylphosphine)palladium(0): 384 mg (3 mol. %, 0.33 mmol)
2M $K_2CO_3$: 22 mL (4 eq)
toluene: 115 mL
column chromatography ($SiO_2$, EE:hexane 1:9)
Yield: 1.7 g (52%)
Melting point: 143° C.
GC-MS: m/z=297 diphenyl(6-(pyren-1-yl)pyridin-3-yl)phosphine oxide (C3)

Figure 16:
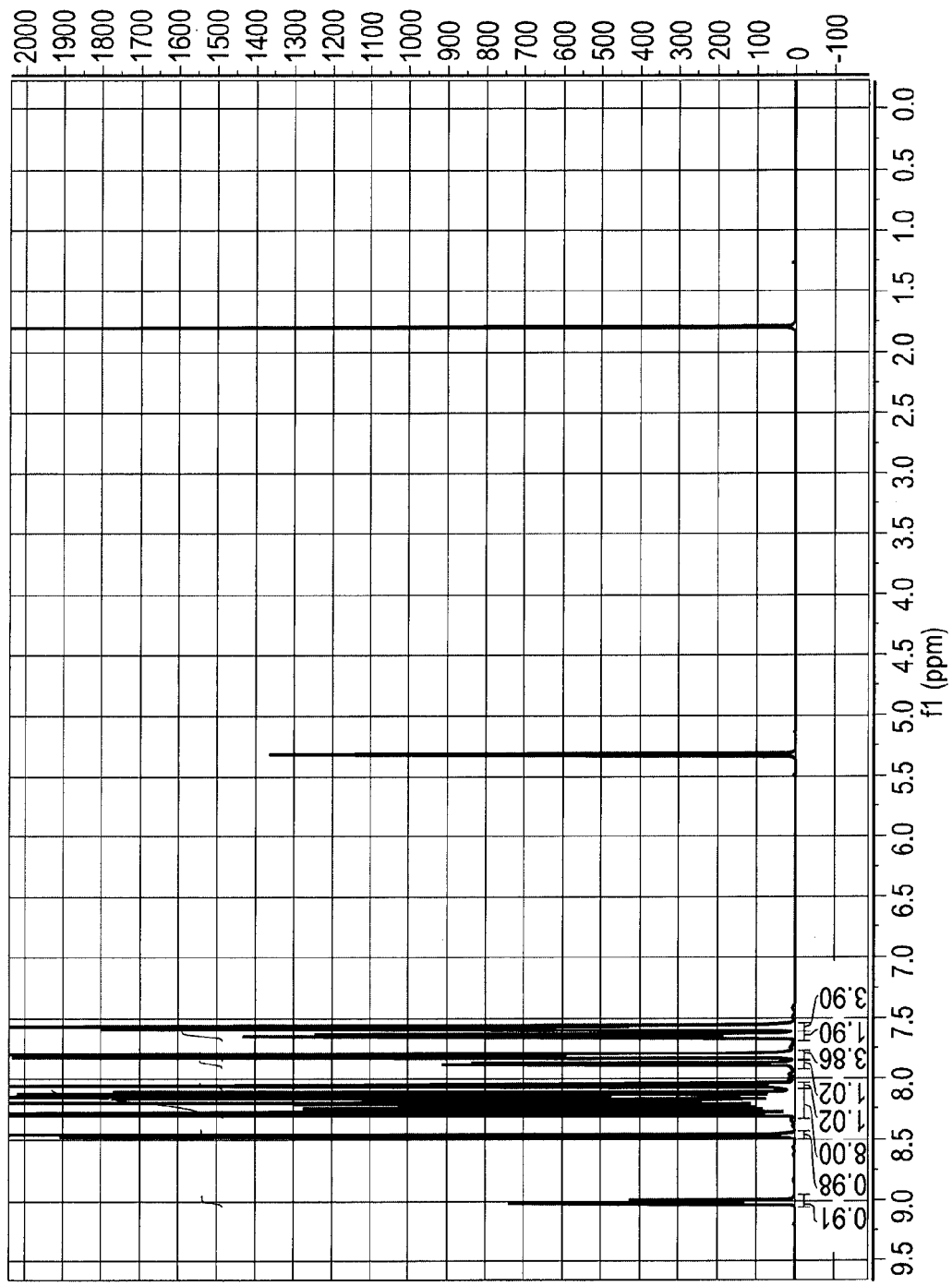
FIG. 16 shows $^1$H NMR spectrum of the comparative compound C3

Synthesis According to General Procedure B 5-fluro-2-(pyren-1-yl)pyridine: 1.46 g (1.0 eq, 4.91 mmol)
0.5M potassiumdiphenylphosphide in THF: 10.3 mL (1.05 eq, 5.16 mmol)
THF: 100 mL
DCM: 60 mL
30 wt. % aqueous $H_2O_2$: 6 mL
column chromatography ($SiO_2$, EE, $R_f$=0.36)
Yield: 1.68 g (71%)
Melting point: 193° C.
EI-MS: m/z=479
$^1$H-NMR: see FIG. 16

((1-(pyridin-2-yl)ethane-1,1-diyl)bis(pyridine-6,2-diyl))bis(diphenylphosphine oxide) (C4)

The synthesis is published in EP 2 452 946.
Compounds C5 and C6 are commercially available.

4,6-di([1,1'-biphenyl]-4-yl)pyrimidine C7

Figure 17:
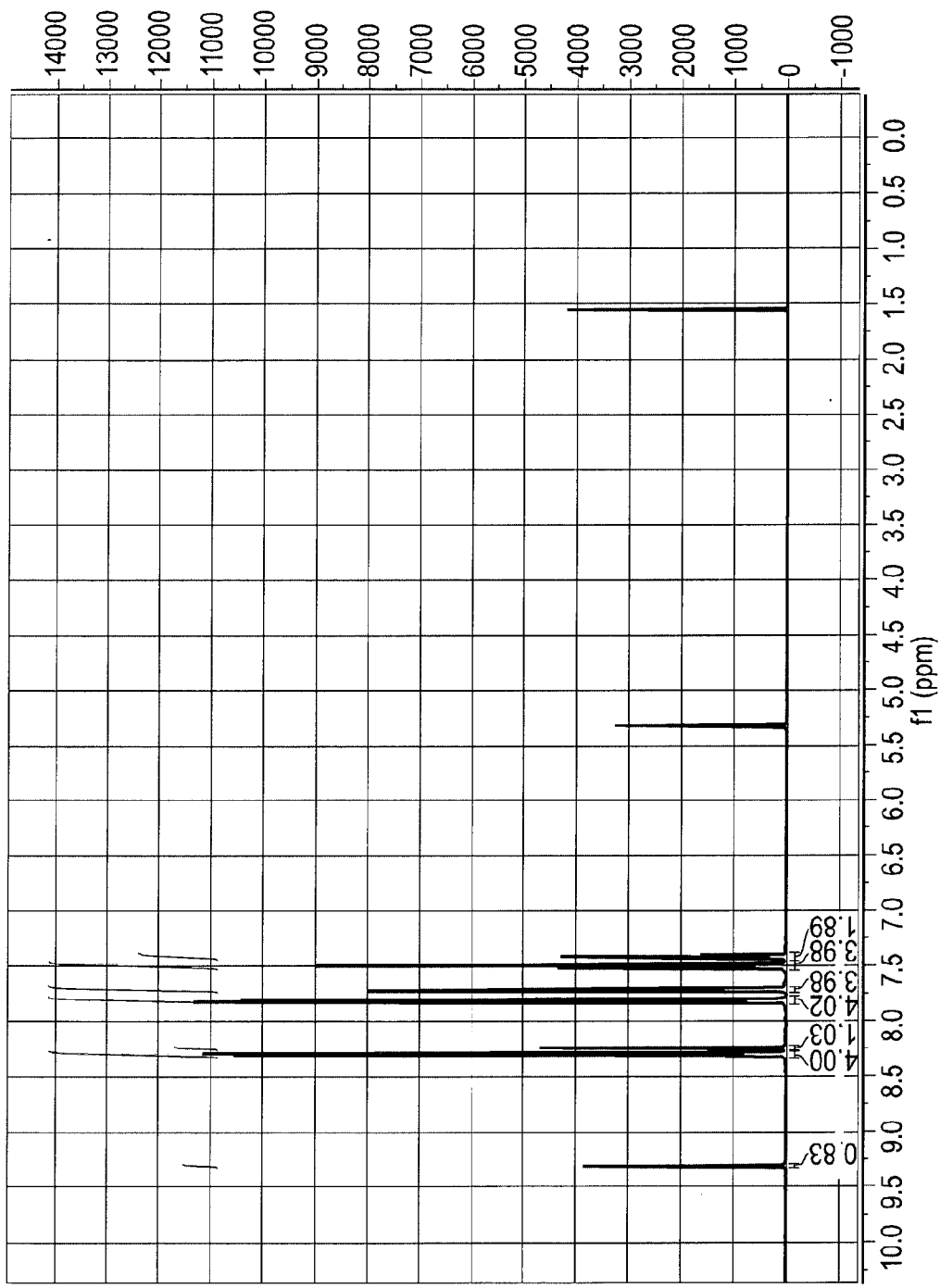
FIG. 17 shows $^1$H NMR spectrum of the comparative compound C7

Synthesis According to General Procedure A 4,6-dichloropyrimidine: 3.0 g (1.0 eq, 20.1 mmol)
4-biphenylboronic acid: 8.8 g (2.2 eq, 44.3 mmol)
Tetrakis(triphenylphosphine)palladium(0): 931 mg (4 mol %, 0.81 mmol)
2M $K_2CO_3$: 40 mL (4 eq)
glyme: 30 mL
column chromatography ($SiO_2$, EE)
Yield: 5.49 g (71%)
Melting point: 224° C.
EI-MS: m/z=384
$^1$H-NMR: see FIG. 17

Device Examples

Example 1

A first blue emitting device was made by depositing a 10 nm layer of HTM1 doped with PD2 (matrix to dopant weight ratio of 92:8 wt. %) onto an ITO-glass substrate, followed by an 130 nm undoped layer of HTM1. Subsequently, a blue fluorescent emitting layer of ABH113 (Sun Fine Chemicals) doped with NUBD370 (Sun Fine Chemicals) (97:3 wt %) was deposited with a thickness of 20 nm. A 36 nm layer of the tested inventive or comparative compound was deposited on the emitting layer together with 50 wt. % D1 as ETL. Subsequently a layer of Al with a thickness of 100 nm was deposited.

The observed voltages and quantum efficiencies at the current density 10 mA/cm² are reported in the Table 1.

Figure 18:
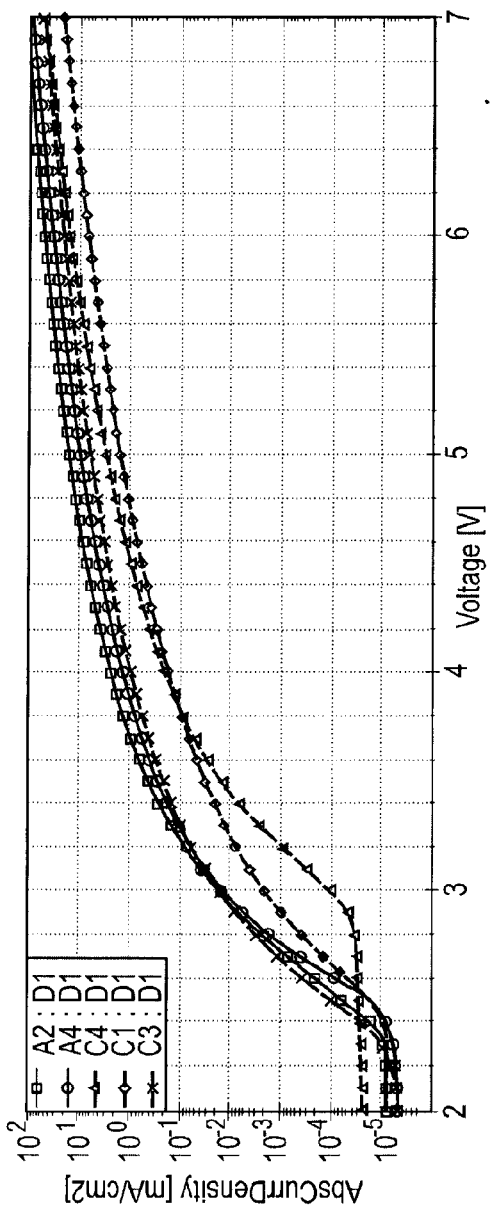
FIG. 18 shows the current density versus applied bias for the inventive and comparative compounds in example 1.
Figure 19:
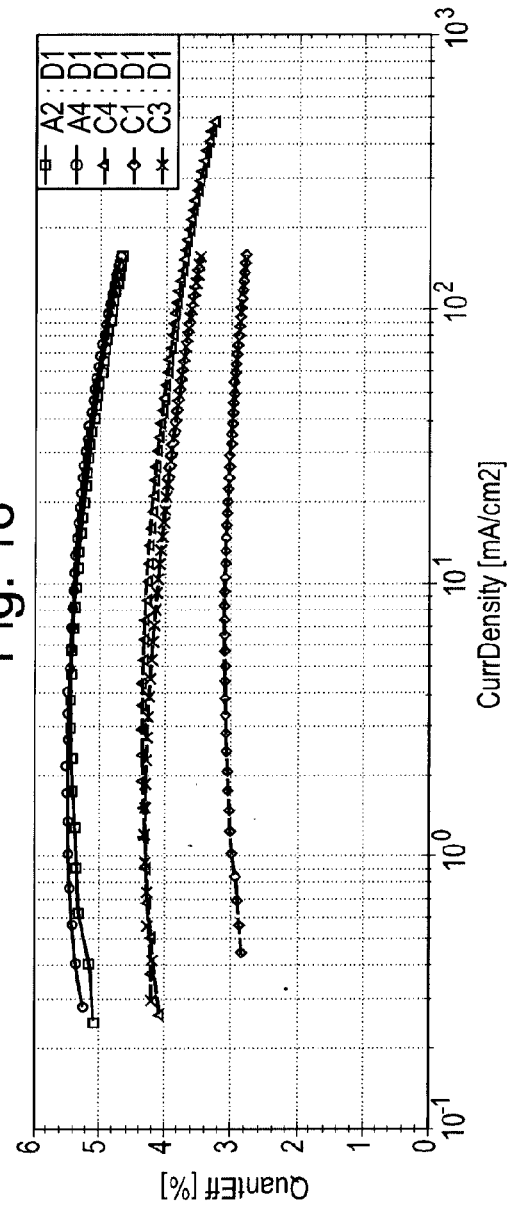
FIG. 19 shows the quantum efficiency versus current density for the inventive and comparative compounds in example 1.

FIG. 18 and FIG. 19 depict OLED performance curves of A2, A4, C4, C1 and C3, clearly showing superior performance (lower voltage, higher efficiency) of inventive compounds over comparative compounds when doped with D1.

Example 2

A similar device was produced as in Example 1, with the difference that the ETL was made of a mixture between the tested inventive or comparative compound and D2 with a weight ratio of 1:1.

The observed voltages and quantum efficiencies at the current density 10 mA/cm² are reported in the Table 1.

Figure 20:
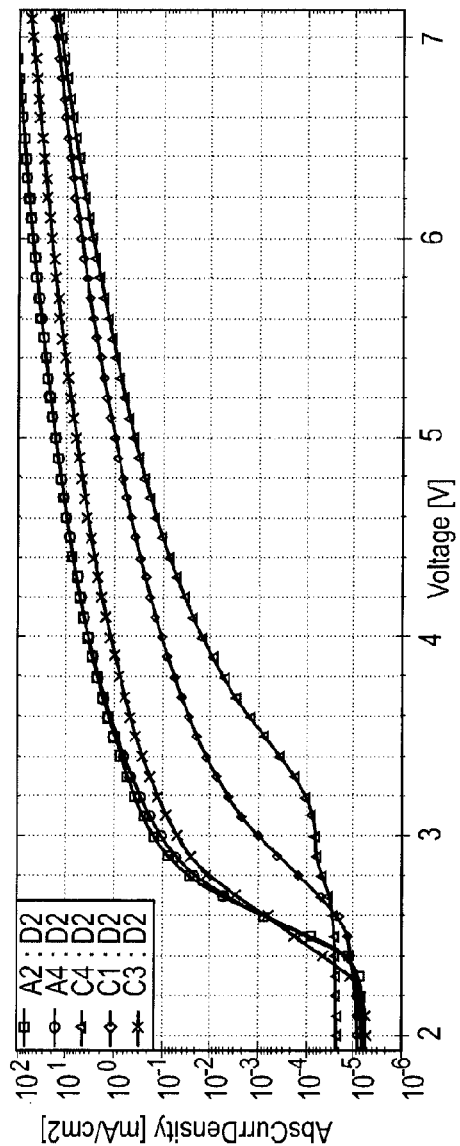
FIG. 20 shows the current density versus applied bias for the inventive and comparative compounds in example 2.
Figure 21:
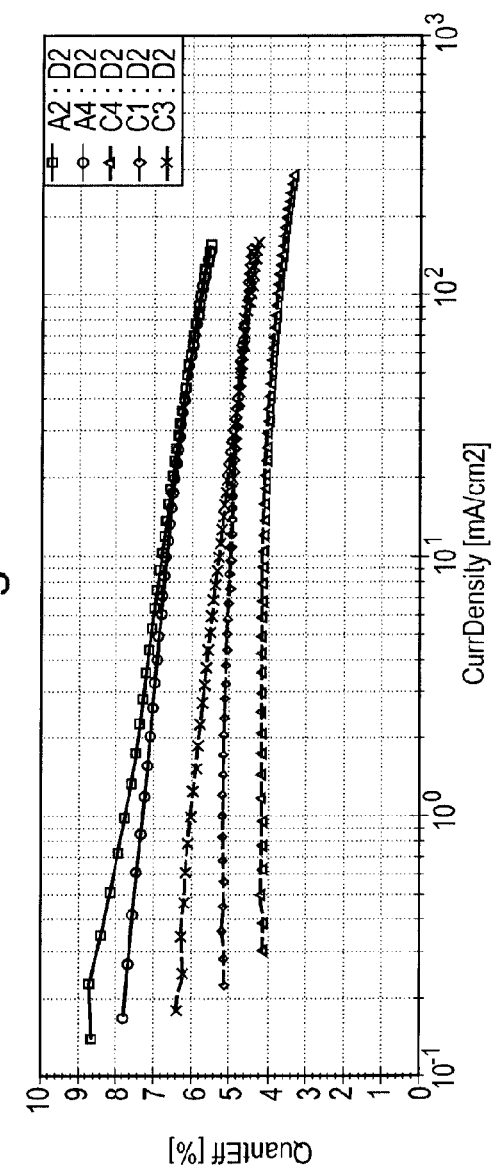
FIG. 21 shows the quantum efficiency versus current density for the inventive and comparative compounds in example 2.

FIG. 20 and FIG. 21 depict OLED performance curves of A2, A4, C4, C1 and C3, clearly showing superior performance (lower voltage, higher efficiency) of inventive compounds over comparative compounds when doped with D2.

Example 3

A similar device was produced as in Example 1, with the difference that the ETL was made of a mixture between the tested inventive or comparative compound and D3 with a weight ratio of 3:1.

The observed voltages and quantum efficiencies at the current density 10 mA/cm² are reported in the Table 1.

Figure 22:
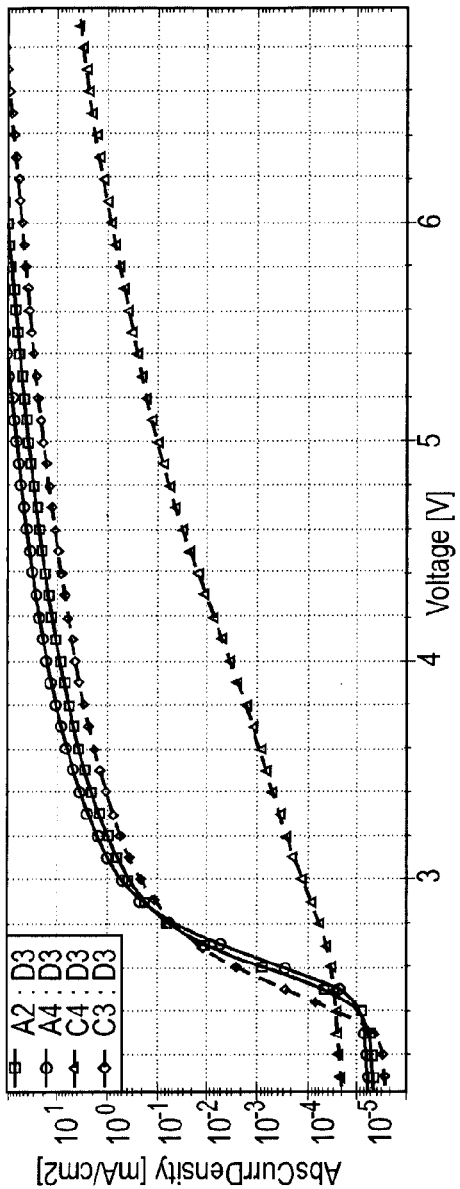
FIG. 22 shows the current density versus applied bias for the inventive and comparative compounds in example 3.
Figure 23:
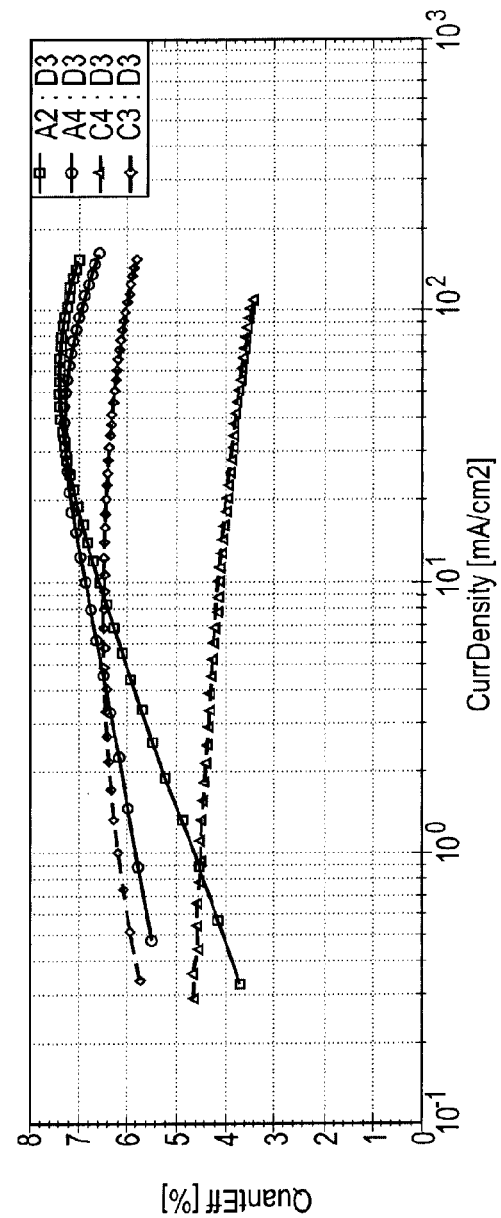
FIG. 23 shows the quantum efficiency versus current density for the inventive and comparative compounds in example 3.

FIG. 22 and FIG. 23 depict OLED performance curves of A2, A4, C4 and C3, clearly showing superior performance (lower voltage, higher efficiency) of inventive compounds over comparative compounds when doped with D3.

The features disclosed in the foregoing description, in the claims and in the accompanying drawings may both separately and in any combination be material for realizing the invention in diverse forms thereof.

Used Abbreviations

CV cyclovoltammetry
DCM dichloromethane
DSC differential scanning calorimetry
EE ethylester (ethyl acetate)
$Fc^+$/Fc ferrocenium/ferrocene reference system
HPLC high performance liquid chromatography
NMR nuclear magnetic resonance
SPS solvent purification system
TGA thermogravimetry thermal analysis
THF tetrahydrofuran
TLC thin layer chromatography
UV UV/Vis spectroscopy
eq chemical equivalent
mol. % molar percent
wt. % weight (mass) percent

The invention claimed is:
1. A semiconducting material comprising at least one salt or complex of a metal cation, and a compound according to formula (I):

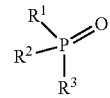

wherein $R^1$, $R^2$ and $R^3$ are independently selected from $C_1$-$C_{30}$-alkyl, $C_3$-$C_{30}$-cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, $C_6$-$C_{30}$-aryloxy, or a structural unit having general formula E-A-,
wherein A is a spacer unit comprising a trivalent nitrogen atom having a lone electron pair, wherein the spacer unit has a structure which allows formation of a 5-, 6- or 7-membered chelate ring with the metal cation, wherein the chelate ring comprises the oxygen atom of formula (I) and the trivalent nitrogen atom of the spacer unit coordinated to the metal cation, and E is an electron transporting unit comprising a conjugated system of at least 10 delocalized electrons, and wherein at least one group selected from $R^1$, $R^2$ or $R^3$ is E-A-, wherein the electron transport unit E in the at least one group selected from $R^1$, $R^2$, and $R^3$ is selected from the group consisting of biphenyl, bithienyl, phenylthiophene, phenylpyridine, and an aromatic or heteroaromatic skeleton having at least two condensed aromatic rings.

2. The semiconducting material according to claim 1, wherein the metal cation is a cation of a metallic element selected from the main groups of the Periodic Table.

3. The semiconducting material according to claim 2, wherein the metallic element is selected from the first or second main group of the Periodic Table.

4. The semiconducting material according to claim 1, wherein the spacer A is a divalent six-membered aromatic heterocyclic group.

5. The semiconducting material according to claim 4, wherein the spacer A is selected from azine-2,4-diyl, azine-2,5-diyl, azine-2,6-diyl, 1,3-diazine-2,4-diyl, or 1,3-diazine-2,5-diyl.

6. The semiconducting material according to claim 1, wherein the electron transporting unit E is a $C_{14}$-$C_{50}$-aryl or a $C_8$-$C_{50}$ heteroaryl.

7. The semiconducting material according to claim 1, wherein in the compound of formula (I), the group E-A- is a group represented by the following formula:

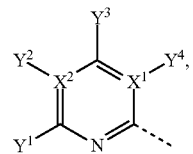

wherein the dashed line represents the single bond to the phosphorus atom,
$Y^1$ and $Y^3$ are independently selected from H, $C_6$-$C_{50}$ aryl, $C_3$-$C_{50}$ heteroaryl, or P(O)$R^4R^5$;
$Y^2$ and $Y^4$ are independently selected from H, $C_6$-$C_{50}$ aryl, or $C_3$-$C_{50}$ heteroaryl;
$R^4$ and $R^5$ are independently selected from $C_6$-$C_{30}$ aryl, $C_3$-$C_{30}$ cycloalkyl, or $C_3$-$C_{30}$ heteroaryl,
$X^1$ and $X^2$ are independently selected from C and N, with the proviso that
i) both $X^1$ and $X^2$ are not N at the same time, and if any of $X^1$ and $X^2$ is N, the adjacent Y is an electron lone pair,
ii) none of $Y^1$ and $Y^3$ is P(O)$R^4R^5$ if any of $X^1$ and $X^2$ is N, and
iii) at least one of $Y^1$, $Y^2$, $Y^3$, or $Y^4$ is a 1,1'-biphenylyl or comprises at least two condensed aromatic rings.

8. The semiconducting material according to claim 7, wherein at least two groups selected from $Y^1$, $Y^2$, $Y^3$ and $Y^4$ are H.

9. The semiconducting material according to claim 1, wherein the metal cation is selected from Li$^+$ and Mg$^{2+}$.

10. The semiconducting material according to claim 1, wherein the salt of the metal cation is selected from 8-hydroxyquinolinolate, pyrazolylborate, or phenolate substituted with a phosphine oxide group.

11. An electronic device comprising a cathode, an anode, and the semiconducting material according to claim 1, wherein the semiconducting material is arranged between the cathode and the anode.

12. The electronic device according to claim 11, further comprising an electron transporting layer or an electron injecting layer, wherein the semiconducting material is present in the electron transporting layer or the electron injecting layer.

13. The electronic device according to claim 11, wherein the electronic device is a light emitting device.

14. A compound having the structure according to formula (I):

wherein $R^1$, $R^2$ and $R^3$ are independently selected from $C_1$-$C_{30}$-alkyl, $C_3$-$C_{30}$-cycloalkyl, $C_2$-$C_{30}$-heteroalkyl, $C_6$-$C_{30}$-aryl, $C_2$-$C_3$O-heteroaryl, $C_1$-$C_{30}$-alkoxy, $C_3$-$C_{30}$-cycloalkyloxy, or $C_6$-$C_{30}$-aryloxy,
at least one of $R^1$, $R^2$ and $R^3$ is a group represented by the following formula—

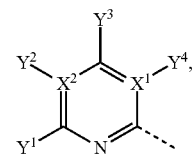

wherein the dashed line represents the single bond to the phosphorus atom of formula (I),
$Y^1$ and $Y^3$ are independently selected from H, phenyl, naphtyl, 1,1'-biphenylyl, quinolinyl, anthracenyl, phenanthrenyl, pyrenyl, or P(O)$R^4R^5$;
$Y^2$ and $Y^4$ are independently selected from H, phenyl, naphtyl, 1,1'-biphenylyl, quinolinyl, anthracenyl, phenanthrenyl, or pyrenyl;
$R^4$ and $R^5$ are independently selected from $C_6$-$C_{30}$ aryl, $C_3$-$C_{30}$ cycloalkyl, or $C_3$-$C_{30}$ heteroaryl,
$X^1$ and $X^2$ are independently selected from C and N, with the proviso that
iv) both $X^1$ and $X^2$ are not N at the same time, and if any of $X^1$ and $X^2$ is N, the adjacent Y is an electron lone pair,
v) none of $Y^1$ and $Y^3$ is P(O)$R^4R^5$ if any of $X^1$ and $X^2$ is N, and
vi) at least one of $Y^1$, $Y^2$, $Y^3$, or $Y^4$ is 1,1'-biphenylyl or comprises at least two condensed aromatic rings.

15. The compound according to claim 14, wherein the compound of formula (I) has the structure (Ia) or (Ib):

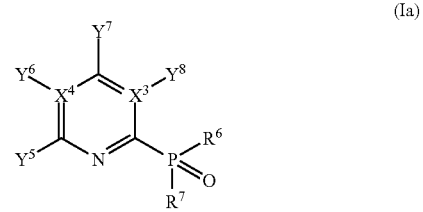

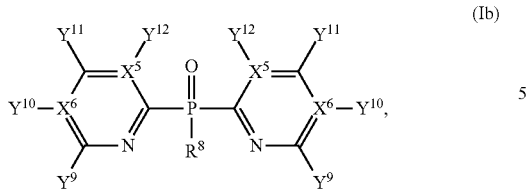

wherein $R^6$, $R^7$ and $R^8$ are independently selected from $C_6$-$C_{30}$ aryl, $C_3$-$C_{30}$ cycloalkyl, or $C_3$-$C_{30}$ heteroaryl, $Y^5$, $Y^7$, $Y^9$ and $Y^{11}$ are independently selected from H, $C_6$-$C_{50}$ aryl, $C_3$-$C_{50}$ heteroaryl, or $P(O)R^4R^5$, $Y^6$, $Y^8$, $Y^{10}$ and $Y^{12}$ are independently selected from H, $C_6$-$C_{50}$ aryl, or $C_3$-$C_{50}$ heteroaryl, $X^3$, $X^4$, $X^5$ and $X^6$ are independently selected from C and N, with the proviso that i) both $X^3$ and $X^4$ or both $X^5$ and $X^6$ are not N at the same time, and if any of $X^3$ and $X^4$ or any of $X^5$ and $X^6$ is N, the adjacent Y is an electron lone pair, ii) neither $Y^5$ nor $Y^7$ and neither $Y^9$ nor $Y^{11}$ is $P(O)R^4R^5$ if any of $X^3$ and $X^4$ or any of $X^5$ and $X^6$ is N, and iii) at least one of $Y^5$, $Y^6$, $Y^7$, or $Y^8$ and at least one of $Y^9$, $Y^{10}$, $Y^{11}$, or $Y^{12}$ is 1,1'-biphenylyl or comprises at least two condensed aromatic rings.

* * * * *